(12) United States Patent
Kammer et al.

(10) Patent No.: US 8,309,891 B2
(45) Date of Patent: Nov. 13, 2012

(54) ADAPTER FOR USE WITH A LIQUID WARMING DEVICE

(75) Inventors: Patrick Kammer, Greensboro, NC (US); Kevin Joseph Rackers, Summerfield, NC (US); Mark Martel, Belews Creek, NC (US); Todd Cassidy, Mocksville, NC (US)

(73) Assignee: C Change Surgical LLC, Winston-Salem, NC (US)

( * ) Notice: Subject to any disclaimer, the term of this patent is extended or adjusted under 35 U.S.C. 154(b) by 885 days.

(21) Appl. No.: 11/906,188

(22) Filed: Oct. 1, 2007

(65) Prior Publication Data
US 2008/0152937 A1 Jun. 26, 2008

Related U.S. Application Data

(63) Continuation-in-part of application No. 11/378,531, filed on Mar. 17, 2006, which is a continuation-in-part of application No. 11/209,283, filed on Aug. 23, 2005, now Pat. No. 7,128,275, application No. 11/906,188, which is a continuation-in-part of application No. 29/285,362, filed on Mar. 28, 2007, now Pat. No. Des. 568,989, which is a continuation-in-part of application No. 29/226,137, filed on Mar. 24, 2005, now Pat. No. Des. 546,943, application No. 11/906,188, which is a continuation-in-part of application No. 11/209,430, filed on Aug. 23, 2005, now Pat. No. 7,560,667, and a continuation-in-part of application No. 11/209,442, filed on Aug. 23, 2005, now Pat. No. 7,459,657.

(60) Provisional application No. 60/848,440, filed on Sep. 29, 2006, provisional application No. 60/603,956, filed on Aug. 24, 2004, provisional application No. 60/603,957, filed on Aug. 24, 2004.

(51) Int. Cl.
*A61B 19/00* (2006.01)
*A61B 19/02* (2006.01)
*A61F 7/00* (2006.01)
(52) U.S. Cl. .................. 219/433; 219/432; 220/23.89
(58) Field of Classification Search ............... 220/23.89
See application file for complete search history.

(56) References Cited

U.S. PATENT DOCUMENTS
189,590 A 4/1877 Wright
(Continued)

OTHER PUBLICATIONS

"Clinical Guideline for the Prevention of Unplanned Perioperative Hypothermia", American Society of PeriAnesthesia Nurses, 15 pgs., published approx. Oct. 2002, www.aspan.org.
(Continued)

*Primary Examiner* — Joseph M Pelham
(74) *Attorney, Agent, or Firm* — Andrew D. Sorensen; Shaoni L. Mitchell

(57) ABSTRACT

A liquid warming device for heating sterile fluids in a removable container is described with emphasis on the properties of the container interaction with the liquid warming device and with a drape that works with the container to maintain a sterile field above the drape and the top of the container. The interactions between a temperature sensor and a temperature well integrated in the removable container are disclosed. Also disclosed are various desirable aspects for a control system for a liquid warming device are provided. The liquid warming device can selectively employ a adapter in order to receive a container limited to a smaller diameter than the largest container diameter that can be accommodated by the liquid warming device. The small diameter container may receive a volume of sterile fluid so that the liquid warming device can maintain the sterile fluid in the small diameter container within a prescribed range of temperatures above ambient air temperature.

11 Claims, 22 Drawing Sheets

U.S. PATENT DOCUMENTS

| | | | |
|---|---|---|---|
| 199,370 A | 1/1878 | Kearns | |
| 255,165 A | 3/1882 | Hale | |
| 269,054 A | 12/1882 | Hemsteger | |
| 298,287 A | 5/1884 | Cochran et al. | |
| 1,797,963 A | 3/1931 | Neller | |
| 1,811,896 A | 6/1931 | Ross | |
| 2,546,104 A * | 3/1951 | MacGregor | 126/377.1 |
| 2,682,602 A | 6/1954 | Huck | |
| 2,892,066 A | 6/1959 | Springer | |
| 2,994,761 A | 8/1961 | Hart et al. | |
| 3,031,565 A | 4/1962 | Appleton et al. | |
| 3,374,936 A | 3/1968 | Colato | |
| 3,698,594 A | 10/1972 | Boehlert | |
| 3,751,629 A | 8/1973 | Eisler | |
| 3,767,898 A | 10/1973 | Wells et al. | |
| 3,974,358 A | 8/1976 | Goltsos | |
| 4,419,568 A | 12/1983 | Van Overloop | |
| 4,700,050 A | 10/1987 | Hennuy et al. | |
| D298,452 S | 11/1988 | Carter | |
| 4,934,152 A | 6/1990 | Templeton | |
| 4,967,057 A | 10/1990 | Bayless et al. | |
| 4,967,061 A | 10/1990 | Weber, Jr. et al. | |
| 5,129,033 A | 7/1992 | Ferrara et al. | |
| 5,174,306 A | 12/1992 | Marshall | |
| 5,271,085 A | 12/1993 | Carballo | |
| 5,331,820 A | 7/1994 | Faries, Jr. et al. | |
| 5,400,616 A | 3/1995 | Faries, Jr. et al. | |
| 5,415,180 A | 5/1995 | Horan | |
| 5,435,322 A | 7/1995 | Marshall | |
| 5,451,747 A | 9/1995 | Sullivan et al. | |
| 5,549,543 A * | 8/1996 | Kim | 600/169 |
| 5,551,240 A | 9/1996 | Faries, Jr. et al. | |
| 5,615,423 A | 4/1997 | Faries, Jr. et al. | |
| 5,653,938 A | 8/1997 | Faries, Jr. et al. | |
| 5,718,124 A | 2/1998 | Senecal | |
| 5,729,653 A | 3/1998 | Magliochetti et al. | |
| 5,862,672 A | 1/1999 | Faries, Jr. et al. | |
| 5,879,621 A | 3/1999 | Faries, Jr. et al. | |
| 6,087,636 A * | 7/2000 | Faries et al. | 219/429 |
| 6,091,058 A | 7/2000 | Faires, Jr. et al. | |
| 6,255,627 B1 | 7/2001 | Faries, Jr. et al. | |
| 6,259,067 B1 | 7/2001 | Faries, Jr. et al. | |
| 6,294,762 B1 | 9/2001 | Faries, Jr. et al. | |
| 6,371,121 B1 | 4/2002 | Faries, Jr. et al. | |
| 6,384,380 B1 | 5/2002 | Faries, Jr. et al. | |
| 6,392,206 B1 | 5/2002 | Von Arx et al. | |
| 6,401,602 B1 | 6/2002 | Lin | |
| 6,433,317 B1 | 8/2002 | Arx et al. | |
| 6,457,601 B1 | 10/2002 | Chappell | |
| 6,593,552 B1 * | 7/2003 | Li | 219/432 |
| 6,660,974 B2 | 12/2003 | Faries, Jr. et al. | |
| 6,711,989 B1 | 3/2004 | Sarnoff | |
| 6,768,085 B2 | 7/2004 | Faries, Jr. et al. | |
| 6,860,271 B2 | 3/2005 | Faries, Jr. et al. | |
| 6,884,970 B2 * | 4/2005 | Lehman | 219/432 |
| 6,910,485 B2 | 6/2005 | Faires, Jr. et al. | |
| 6,918,395 B2 | 7/2005 | Faries, Jr. et al. | |
| 6,927,365 B2 * | 8/2005 | Li | 219/432 |
| 7,128,275 B2 | 10/2006 | Kammer et al. | |
| 7,176,030 B2 | 2/2007 | Faries, Jr. et al. | |
| D546,943 S | 7/2007 | Kammer et al. | |
| D546,944 S | 7/2007 | Kammer et al. | |
| D547,444 S | 7/2007 | Kammer et al. | |
| D568,989 S | 5/2008 | Kammer et al. | |
| D569,970 S | 5/2008 | Kammer et al. | |
| 7,671,302 B1 * | 3/2010 | Faries et al. | 219/429 |
| 7,728,262 B1 * | 6/2010 | Faries et al. | 219/429 |
| 2001/0045188 A1 | 11/2001 | Tesngas | |
| 2002/0043260 A1 | 4/2002 | Layer et al. | |
| 2002/0188259 A1 | 12/2002 | Hickle et al. | |
| 2003/0230588 A1 | 12/2003 | Zepter | |
| 2004/0065314 A1 | 4/2004 | Layer et al. | |
| 2005/0242086 A1 | 11/2005 | Imura | |
| 2005/0267425 A1 | 12/2005 | Castora et al. | |
| 2006/0011608 A1 | 1/2006 | Lehman | |
| 2006/0065276 A1 | 3/2006 | Kammer et al. | |
| 2006/0086361 A1 | 4/2006 | Kammer et al. | |

OTHER PUBLICATIONS

Sessler et al., "Nonpharmacological Prevention of Surgical Would Infections", Clinical Infectious Diseases, CID 2002:35 (Dec. 1) pp. 1397-1404. Published electronically Nov. 13, 2002 by Infectious Diseases Society of America.

* cited by examiner

Fig. 2
PRIOR ART
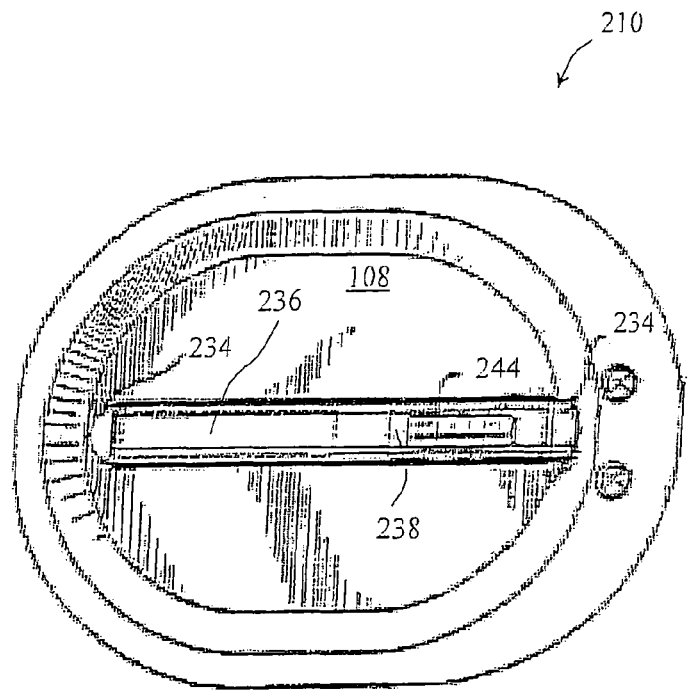
Fig. 2A
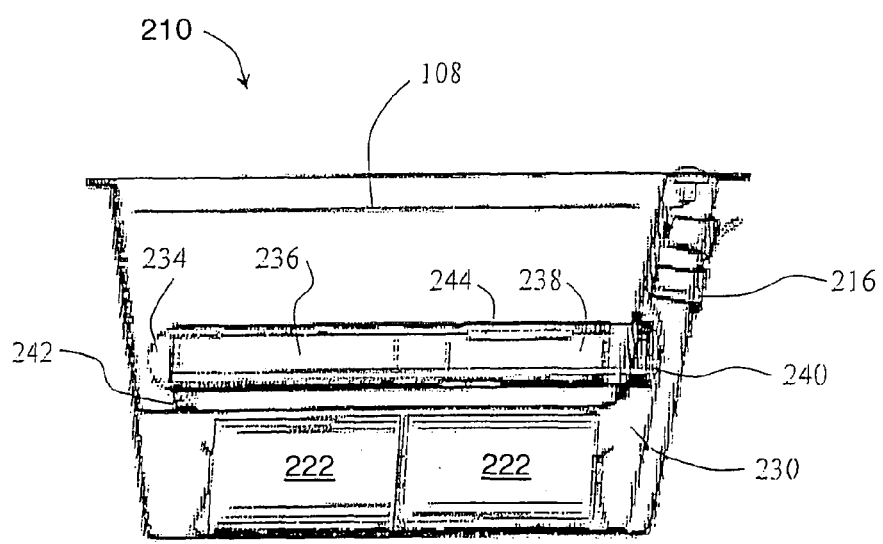
Fig. 2B

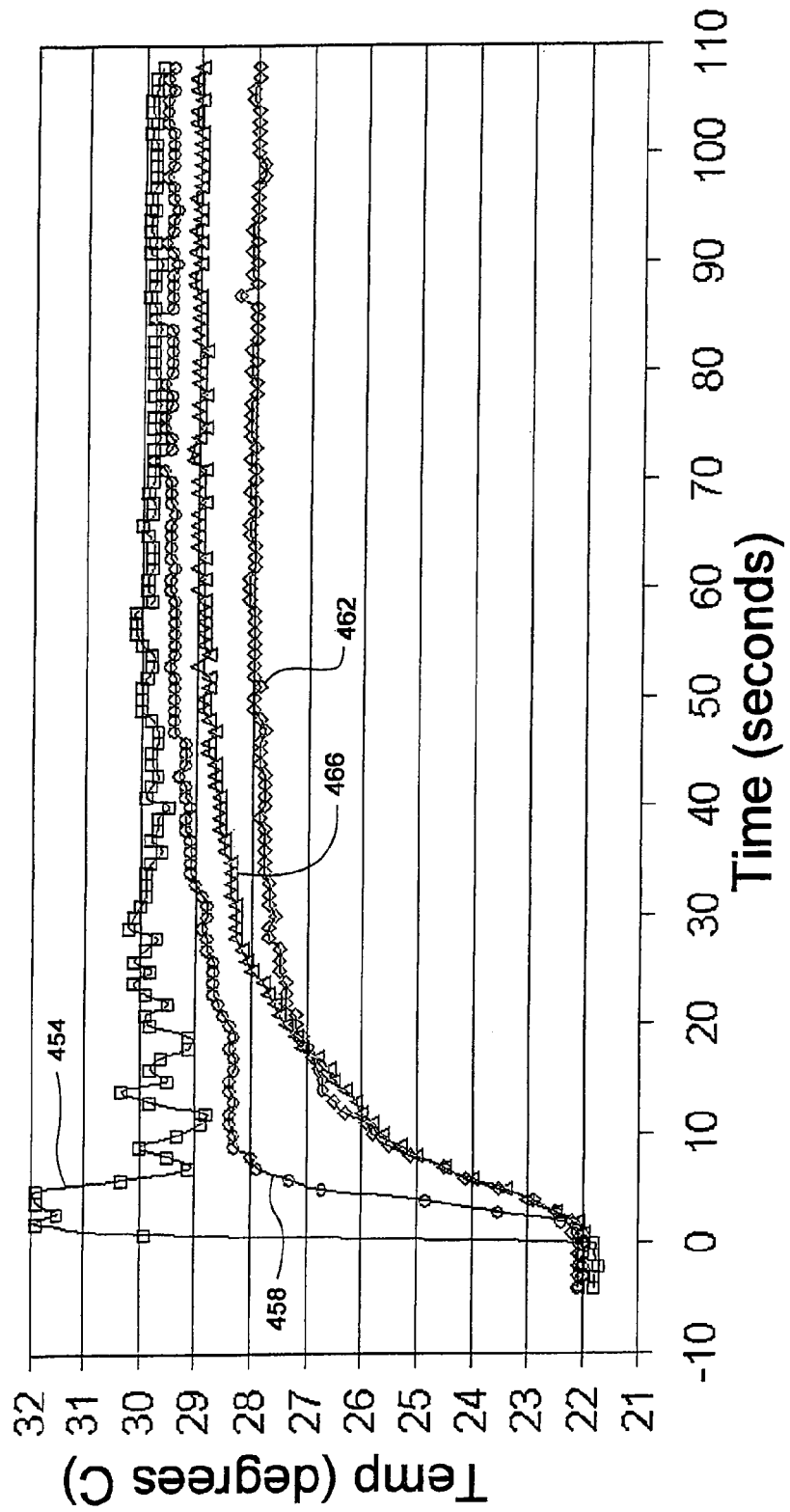

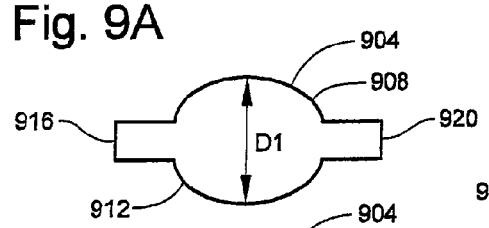
Fig. 9A
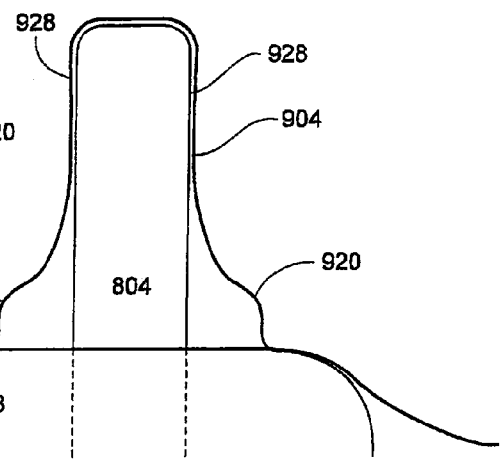
Fig. 9B
Fig. 9C

FIG. 20
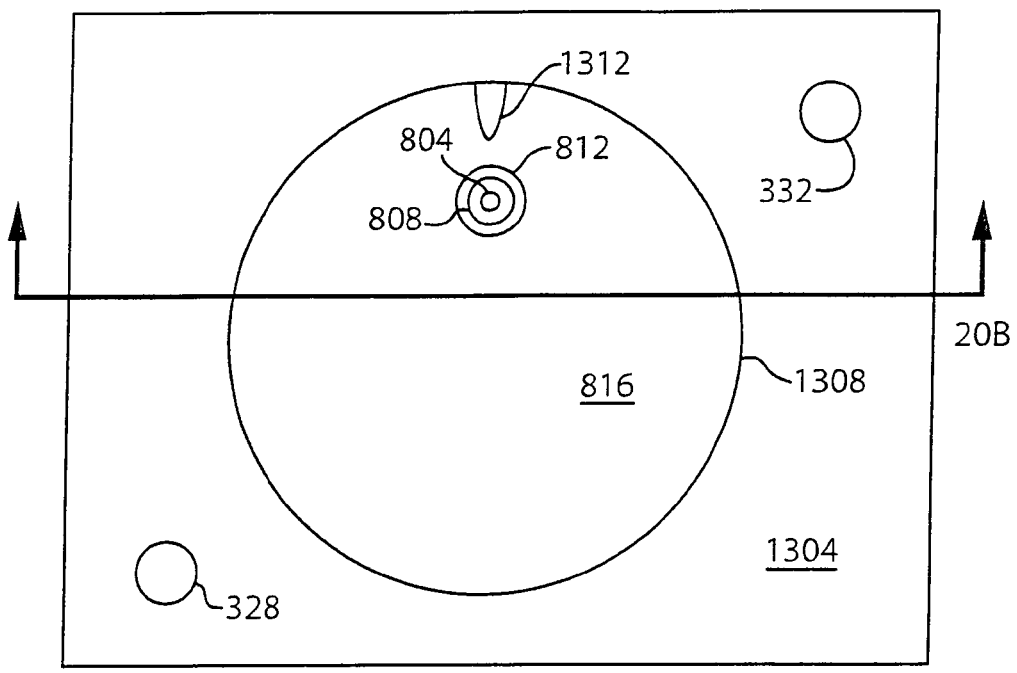
FIG. 20A
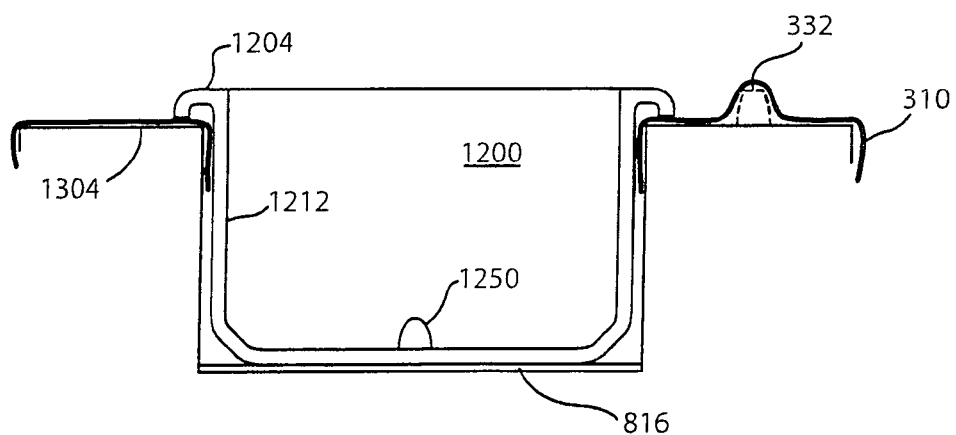
FIG. 20B

FIG. 21
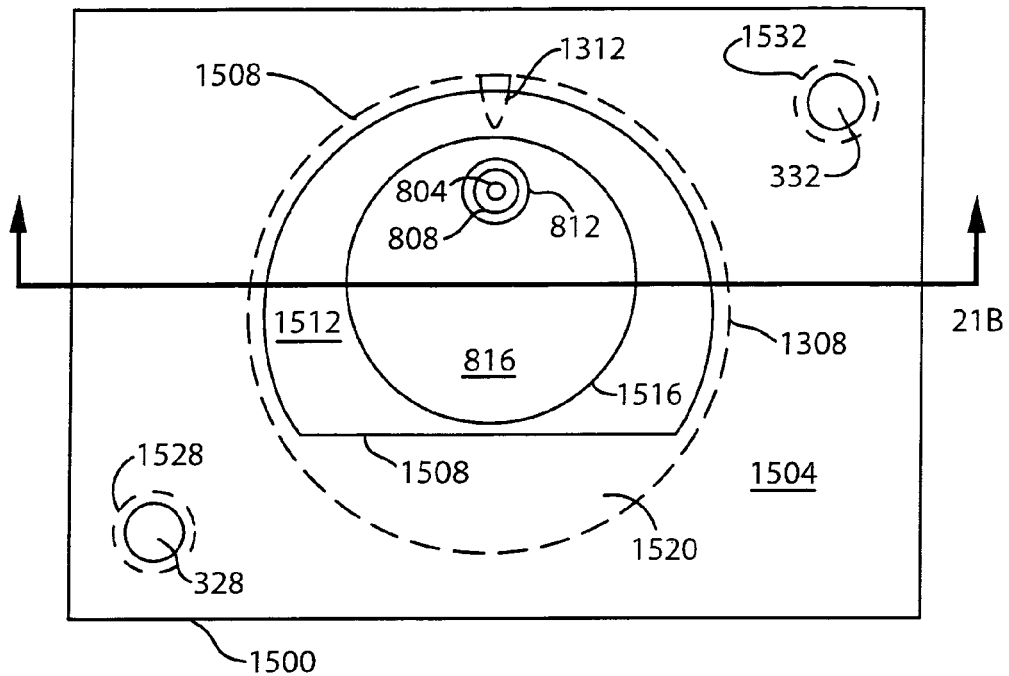
FIG. 21A
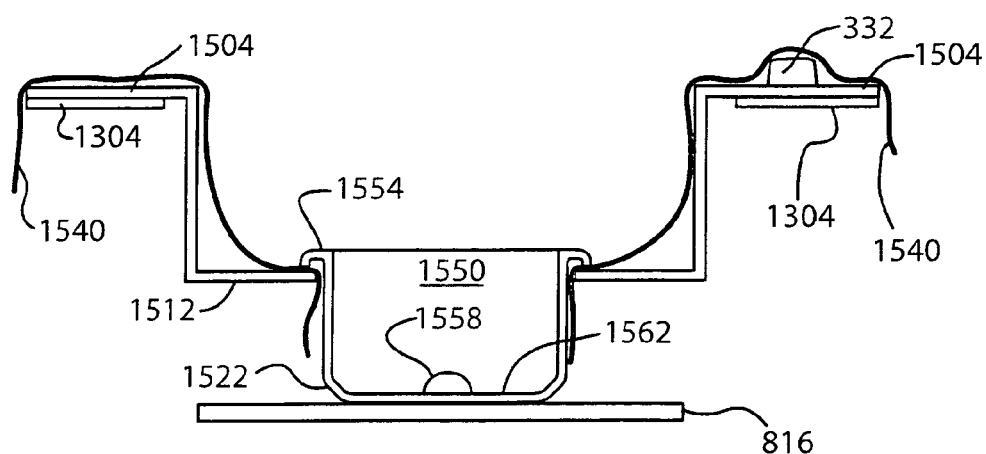
FIG. 21B

FIG. 22
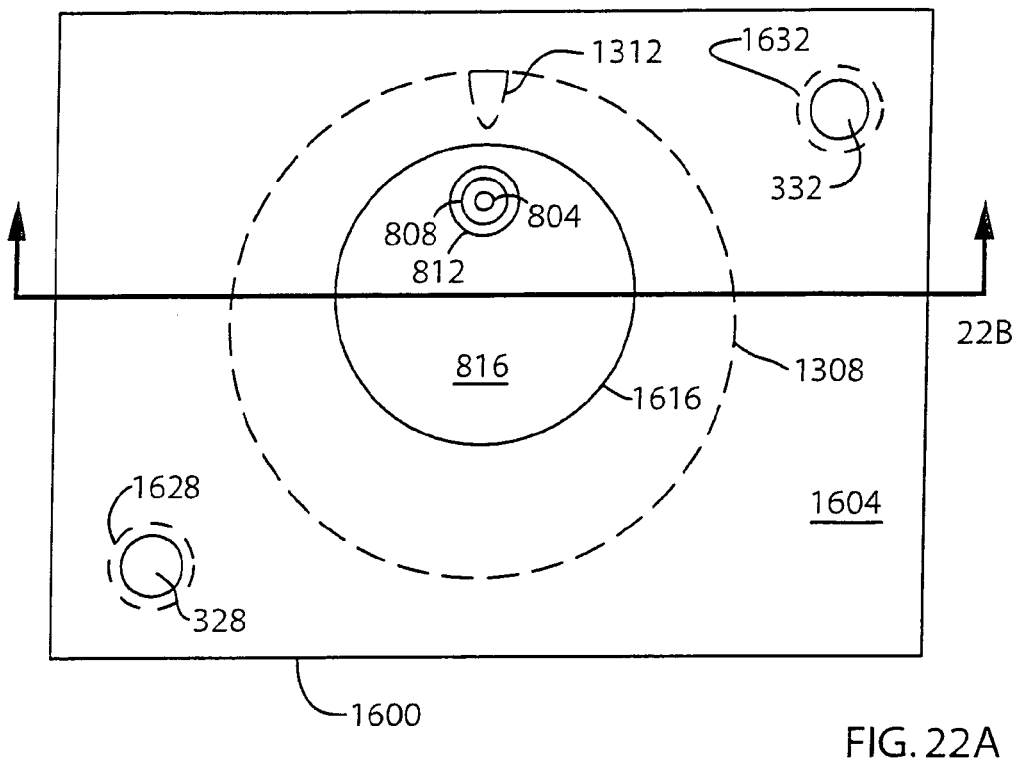
FIG. 22A
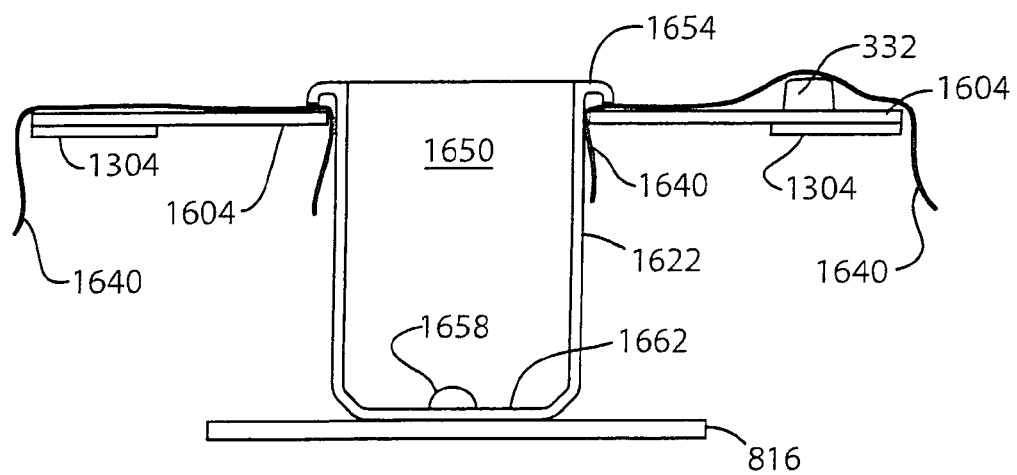
FIG. 22B

FIG. 23
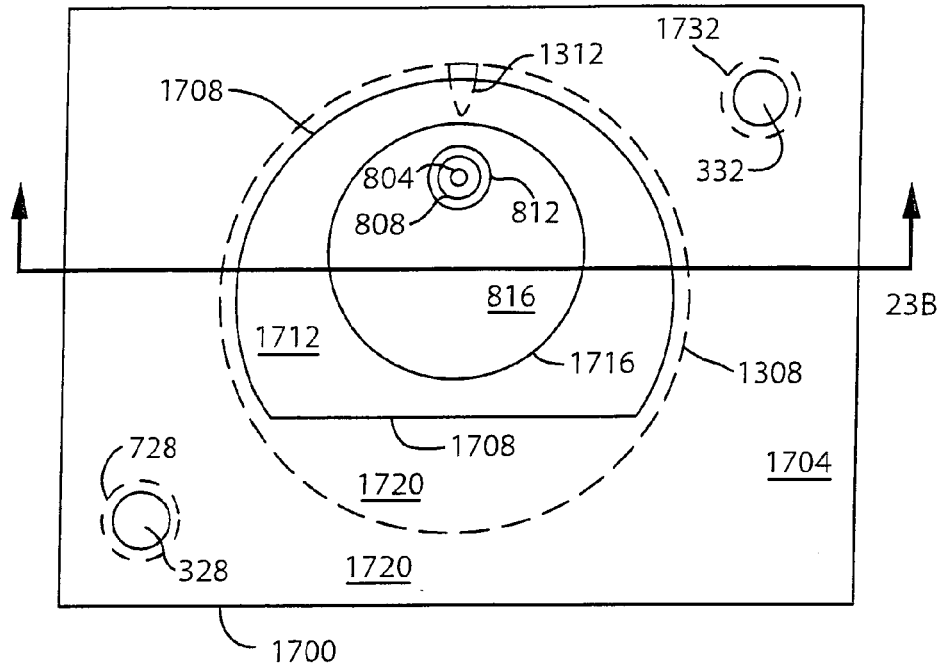
FIG. 23A
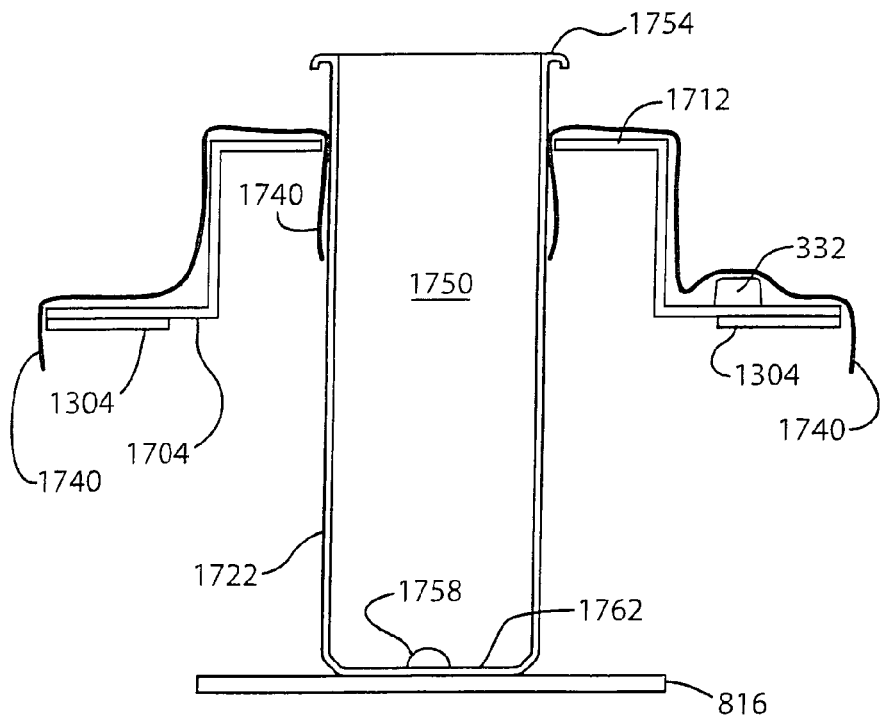
FIG. 23B

ADAPTER FOR USE WITH A LIQUID WARMING DEVICE

This application incorporates by reference and claims priority to a provisional application filed Sep. 29, 2006 for Small Basin Adapter for Use with a Liquid Warming Device with U.S. Ser. No. 60/848,440. This application claims priority to a co-pending U.S. patent application Ser. No. 11/378,531 for Open Access Sleeve for Heated Fluid Units Filed Mar. 17, 2006. Via the '531 application, this application claims priority to and incorporates by reference herein, a U.S. patent application Ser. No. 11/209,283 for Liquid Warming Device with Basin, now U.S. Pat. No. 7,128,275. This application claims priority to and incorporates by reference two provisional patent applications claimed in the '283 application: U.S. Provisional Patent Application 60/603,957 for Heating Element for Liquid Warming Device filed Aug. 24, 2004 and U.S. Provisional Patent Application 60/603,956 for Liquid Warming Device and Control System filed Aug. 24, 2004. This application also claims priority to and incorporates by reference herein U.S. Design patent application Ser. No. 29/285,362 filed Mar. 28, 2007 and its priority document U.S. Design patent application Ser. No. 29/226,137 filed Mar. 24, 2005 for Hospital Basin now U.S. Design Pat. No. D546,943.

This application claims priority to and incorporates by reference herein a co-pending application for a Heating Element for Liquid Warming Device with U.S. Ser. No. 11/209,430. The inventive aspects of heating elements disclosed in that application can be advantageously used with the present invention. This application claims priority to and incorporates by reference herein a co-pending application for a Basin For Use in a Liquid Warming Device with U.S. Ser. No. 11/209,442.

FIELD OF THE DISCLOSURE

This invention relates to improvements in methods and apparatus for heating of sterile surgical liquids.

BACKGROUND OF THE PROBLEMS ADDRESSED

Devices for the heating of sterile surgical liquids are known in the art. In a wide variety of surgical procedures, sterile fluids are used to irrigate the site of the surgery. It is important that the temperature of the fluids used be strictly controlled. As the portion of the brain that regulates body temperature is shut down with anesthesia, it is important that the introduction of sterile fluids does not cool the body core temperature. Clinical studies have indicated that a range of adverse consequences arise from a change in body core temperature as little as one to three degrees Celsius. The adverse consequences from mild perioperative hypothermia include hypertension and increased vascular resistance, cardiac events, coagulopathy, an increase risk of surgical wound infections, and delays in the body's ability to remove drugs from its systems. An additional potential adverse consequence is shivering which can increase metabolic rate up to 500% and thus increase demands for oxygen and the need to clear carbon dioxide. This list of complications is by no means exhaustive, but it highlights the critical importance in controlling the body core temperature. Careful control of the temperature of sterile irrigation fluids is an important part of controlling body core temperature.

The prior art includes various liquid warming devices to warm sterile fluid. Some are incorporated into a rolling cabinet for placement in a convenient place within the sterile field in an operating room so that sterile fluid is available at an appropriate temperature for uses in the surgery such as irrigation or lavage. It is recognized as desirable that the process for heating the fluid be capable of quickly heating the fluid to bring the fluid to the appropriate temperature. It is also recognized that having the heater apply so much heat that it damages the container used to hold the fluid is undesirable. Use of a heater that can expose personnel to heated surfaces that are hot enough to cause injury is undesirable and in some cases contrary to governmental regulations.

A conventional control system used in the art is shown in FIG. 1. A volume of sterile fluid 108 rests on a sterile drape 110 which in turn rests on an integrated basin 104 in the top of the liquid warming device. The sterile drape 110 thus shields the non-sterile liquid warming device from the sterile field. (One of skill in the art will recognize that the weight of the sterile fluid 108 would cause drape 110 to substantially conform to the shape of the integrated basin 104. These drawings are intended to aid the disclosure of concepts, rather than serve as photographs, thus many gaps will exist in order to highlight the discrete elements.)

The integrated basin 104, the drape 110 and the fluid 108 therein are heated by a heater 112 within the liquid warming device. The heater is controlled by measuring the temperature of the heater with a heater temperature detector 116. A heater controller 120 turns the heater on or provides additional current to cause the heater to heat up further if the measured temperature at the heater temperature detector is below a set point 124. As the temperature of the heater is regulated or controlled independently of the actual current temperature of the fluid in the drape, a participant in the surgery will test the temperature of the fluid by sticking a gloved finger 128 into the sterile fluid. This is somewhat effective as the target temperature for the sterile solution is often close to body temperature. If the fluid feels cool to the gloved finger, an instruction is given directly or indirectly to the controller 120 to increase the set point 124 for the heater. A subsequent gloved finger reaction is used to make additional corrections from time to time.

The temperature of the fluid 108 cannot be precisely predicted based on the set point of the last surgery as the temperature will be affected by the pouring of additional fluid into the drape as the fluid added may not be at the target temperature. The fluid temperature may also vary with changes in the positioning of the liquid warming device closer to airflow in the surgical suite, changes in humidity levels, or other factors. As the gloved finger test is rather subjective, it will give different results based on the person giving the test, the body temperature of the person, the length of time the gloved finger is inserted in the fluid, and other factors.

An additional problem in the prior art relates to maintaining the integrity of the sterile field. The integrity of the sterile field is essential to acceptable outcomes during surgery. Any breach that might indicate that the sterile field has become contaminated is taken very seriously. A breach that is undiscovered for a period of time is especially troublesome as it is difficult to assess when the breach was created and whether it caused the patient to be exposed to contaminants while vulnerable during surgery. Thus, it is no wonder that concerns from breaches in the sterile drapes 110 were taken very seriously. U.S. Pat. No. 6,910,485 for Medical Solution Thermal Treatment System and Method of Controlling System Operation in Accordance with Detection of Solution and Leaks in Surgical Drape Container addresses this concern. Likewise, issued U.S. Pat. No. 6,091,058 for Thermal Treatment System and Method for Maintaining Integrity and Ensuring Sterility of Surgical Drapes Used with Surgical Equipment teaches ways of reducing the risk of damage to surgical drapes from objects placed in the drape covered integrated basin.

Thus, problems associated with the recognized risk of a breach in a sterile drape have led others to develop various ways of reducing this risk or at least quickly detecting the breach.

In order to provide peace of mind to those working in the surgical theater, it would be advantageous to provide a way to use a standard disposable removable container or a freestanding metal container with a sufficiently high structural integrity that could be sterilized.

Plastic basins are one type of container and they are ubiquitous in hospitals and are used in many ways. Plastic basins that are sterilized (for example through irradiation or ethylene oxide gas sterilization) can safely be used in the sterile field without a surgical drape placed over them. Metal basins are currently sterilized and safely reused just as a range of surgical implements are sterilized and reused.

The use of such basins would provide peace of mind as it is difficult to conceive of any activity in the sterile field that could cause a breach in a non-defective plastic or metal basin. A secondary benefit would be that standard gradation marks on the inside walls of the sterile removable basin would provide a visual indication of the amount of sterile fluid remaining in the sterile basin. As using basin gradation marks is done by hospital personnel in other contexts, the use of fluid gradation marks in this context will seem familiar.

One attempt to devise a device for heating fluid that used a substantial disposable basin is described in U.S. Pat. No. 5,129,033 for Disposable Thermostatically Controlled Electric Surgical-Medical Irrigation Bowl and Lavage Liquid Warming Bowl and Method of Use. FIGS. 2A and 2B illustrates the top and side views of the device taught in the '033 patent. A warming bowl 210 contains a heater assembly 234 which in turn contains heater 236, thermostat 238, and temperature indicator 244. The heater assembly 234 rests on support 242 and a passageway to an interior core 230 of the warming bowl 210 with the power supply 222.

The apparatus of FIG. 2 is different from FIG. 1 in that the device of FIG. 2 replaces the occasional measurements by gloved finger with continuous monitoring of the fluid temperature with a thermostat 238 placed in the heater assembly 234.

It appears that the intent of the '033 patent is for the entire assembly including the heater assembly 234, power supply 222, and various controls and indicator lights to be disposable as the '033 patent notes that "[i]rrigation liquid bowls are provided in pre-packaged pre-sterilized form ready for use, and they are non-reusable and disposable, in view of the stringent demands on aseptic conditions and also because of the high cost of reliable sterilization for reusable surgical instruments and accessories." Disposing of the electronics with the bowl would seem to make this solution prohibitively expensive.

But, it is hard to see a way to sterilize the '033 device as reuse from surgery to surgery would require a method of reliably sterilizing the heater assembly 234 along with the surface of the bowl that would come in contact with the sterile fluid 108. An additional complication is the need to use a sterilization process that does not impair the hermetic seal 240 as an impaired seal would provide a path for contamination of the inner core 230 and subsequent cross-contamination of the sterile fluid for a later surgery with blood products or other contaminants from an earlier surgery.

A second obvious problem with the solution proposed in the '033 patent is that the heater assembly 234 is simply in the way. Placing the heater assembly 234 in the area meant to contain the sterile fluid 108 solved problems for the design engineers but created lasting problems for the surgical staff who must work around the heater assembly 234 so as to avoid imparting a mechanical shock sufficient of causing the components to fail. The staff must also avoid contact with the heater assembly 234 sufficient to cause a breach in the casing of the heater assembly 234 or in the hermetic seal 240 which might allow fluid to contact non-sterilized areas or to adversely effect the electrical operation. Flooding the inner core 230 could be dangerous to surgical staff if the bowl 210 was using power provided through electrical plug receptacle 216 instead of running off batteries 222.

As noted above, even if the risk of causing a failure to the electrical components or seals is slight, such a risk diminishes the peace of mind of the surgical staff. Adding various detectors to quickly detect various failure modes might increase peace of mind somewhat but at yet another set of added costs to the single-use disposable unit.

The prior art lacks a solution for a fluid heating device using a removable container that provides the benefits of using the actual temperature of the sterile fluid as an input to the control system without incurring the risks and problems inherent in the use of such a temperature probe.

SUMMARY OF THE DISCLOSURE

A liquid warming device with a cavity to receive a removable container is disclosed. In one particular implementation, the liquid warming device uses a container drape with a hole in the drape to allow the bottom portion of the container to extend down below the drape to interact with the liquid warming device while the drape and the top of the container provide a sterile barrier between the top of the liquid warming device and the sterile field. The control system for the liquid warming device operates based on a temperature measurement indicative of the temperature of the liquid contained in the container. The temperature may be sensed by a temperature sensor located in a temperature well that protrudes into the liquid in the container. The invention may be implemented so that the distal end of the temperature sensor engages with the temperature well in an interference fit so that there is good thermal contact between at least a portion of the distal end of the temperature sensor and the interior of the temperature well. A container indicator such as a limit switch actuator and limit switch may be used to confirm the presence of a suitable container before allowing energy to be applied so that energy is not applied unless there is an appropriate container in the proper location in the cavity of the liquid warming device.

In some instances, it may be desirable to provide an adapter so that a liquid warming device that may receive a container with cross sectional area of a first size may receive and hold a container such as a basin that is limited to a second smaller cross sectional area that may be a small fraction of the first size. Another way of looking at this is that it may be desirable to provide an adapter so that a liquid warming device that may receive a first type of container that fits through an opening with a first cross-sectional area in the top of the liquid warming device may be used to heat a second type of container that fits through an opening in a portion of the adapter with a second cross sectional area, less than the first cross sectional area. This smaller container such as a basin may be used with a smaller volume of sterile fluid than the larger container or alternatively may be used with the same volume of fluid as is commonly placed in the large container but with a greater depth of fluid when this is desirable. The container with a smaller cross section may be a fluid container such as container 370 show in FIG. 3 as a round bottle or FIG. 19 as a square bottle. Thus, the range of containers need not be limited to those containers with circular cross sections.

Additional details concerning the invention are disclosed through various examples of implementations which include variations in the container, drape, and the liquid warming device including the control system for the liquid warming device. Although various examples are provided to convey the scope of the invention, it is not appropriate to set forth every possible combination of elements that would fall within the scope of the claims that follow this specification. Those of ordinary skill in the art will recognize that other implementations of this invention can be made using some aspects of one example and other aspects from one or more other examples.

BRIEF DESCRIPTION OF THE DRAWINGS

FIG. 2 includes FIGS. 2A and 2B which illustrate a prior art solution of a disposable device with a temperature sensor permanently suspended in the fluid to be measured.

FIGS. 4A and 4B present experimental data showing how a temperature sensor in a thermocouple well reacts to changes in fluid temperature relative to temperature sensors placed in other locations.

FIGS. 9A, 9B and 9C explain the operation of a thermocouple well using a winged divot to provide an interference fit around a temperature sensor 804.

FIG. 20 which includes drawings 20A and 20B are a top and side view of the components of interest from FIG. 19.

FIGS. 21A and 21B is a top and side view of the components of a first adapter.

FIGS. 22A and 22B is a top and side view of the components of a second adapter.

FIGS. 23A and 23B is a top and side view of the components of a first adapter.

DETAILED DESCRIPTION OF SEVERAL EXAMPLES

The present invention will now be described more fully hereinafter with reference to the accompanying drawings, in order to disclose selected examples of implementations. This invention may, however, be embodied in many different forms and should not be construed as limited to the implementations set forth herein; rather, these implementations are provided so that this disclosure will be thorough and complete, and will fully convey the scope of the invention to those skilled in the art. Like numbers refer to like elements throughout.

Figure 1:
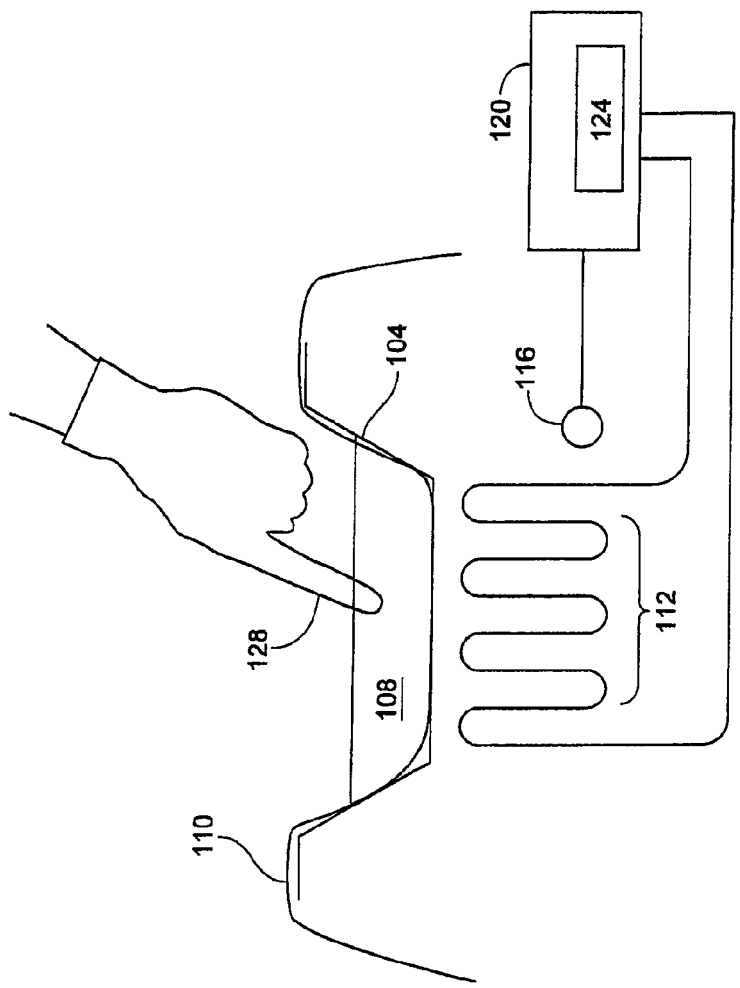
FIG. 1 illustrates a prior art method of controlling fluid temperature by using a gloved finger to sense the temperature and adjusting the heater set point accordingly.
Figure 3:
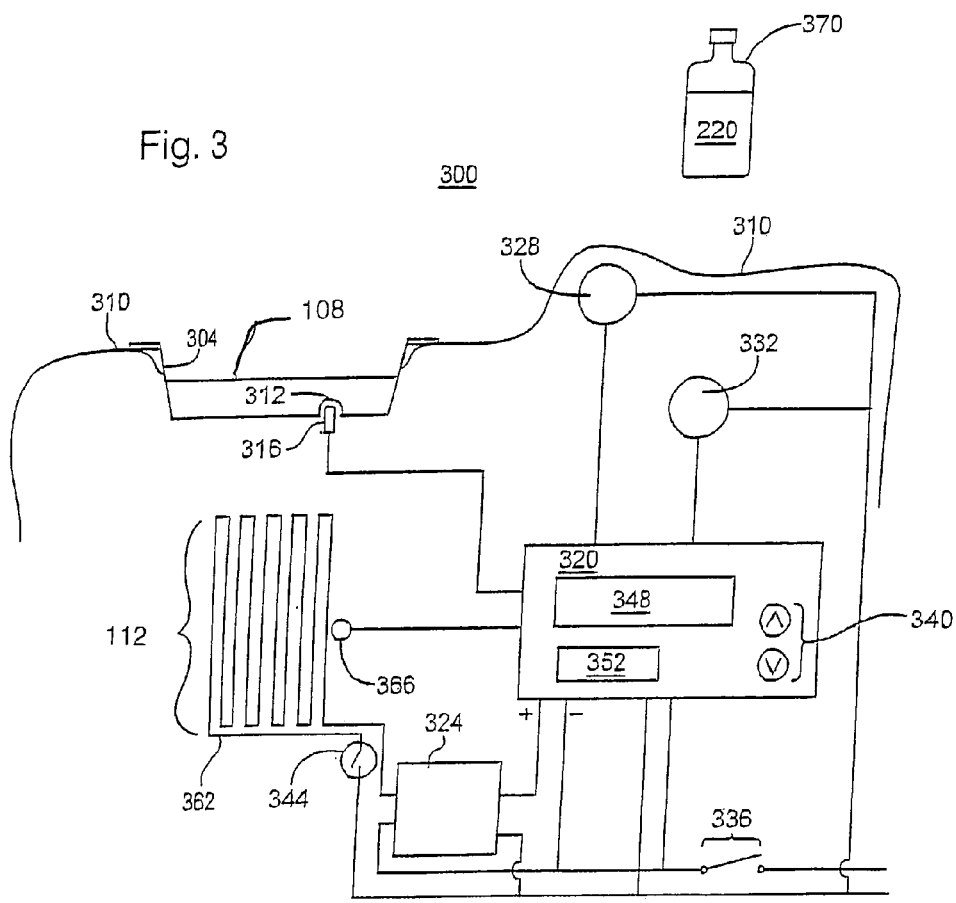
FIG. 3 illustrates one implementation of the present invention including a dual-set point control scheme to control the temperature of fluid 108 in container 304.

FIG. 3 illustrates a first implementation of the present invention. The sterile fluid 108 is inside modified container 304 with integral thermocouple well 312 and temperature sensor 316. Additional sterile fluid 220 may be added as needed from one or more containers 370. Typically, the containers 370 are preheated so that the sterile fluid 220 is close to the temperature desired for sterile fluid 108 as used in the container 304. The heater 112 selectively applies heat that is transferred to the container 304 and the fluid 108. The fluid warming device has a main on/off switch 336. Some heating elements come with a mechanical thermostat 344 such as a bimetallic thermostat to provide a secondary protection against a failed control system. This second mechanical thermostat 344 acts as a switch to shut off the heater if the temperature exceeds a set temperature. This should be set to a temperature that is low enough that the mechanical thermostat opens before the heater can overheat an empty container. For example a mechanical thermostat set for 220 degrees Fahrenheit might be acceptable for use with a container capable of withstanding permanent exposure to a 300 degree Fahrenheit heat source.

In one implementation, a modified surgical drape 310 is connected to some combination of the upper rim of the container 304 or its outside wall so that the container 304 extends down through the hole in the surgical drape. As the modified surgical drape 310 does not run along the bottom of the container, the drape 310 does not interfere with the interaction of the thermocouple well 312 and the control system. Nor does the drape 310 get between the bottom of the container 304 and the heat coming from heater 112 to the bottom of the container. The drape container combination would typically be combined together as part of preparing a surgical kit and the drape would encircle the container bottom with the remainder of the drape folded or pooled in the cavity of the container so that the container could be placed into the fluid warming device and once properly positioned, the drape could be unfolded from the container to cover the top and upper sides of the fluid warming device to maintain a sterile field.

The interaction between the drape 310 and the container 304 could be a simple interference fit such that the container once inserted into a hole in the drape stretches the drape so that the drape stays attached to the container sufficiently for it to maintain the sterile field. Alternatively, the drape could be bonded to the outer wall of the container or to the underside of the rim of the container.

FIG. 3 shows drape 310 extending downward to cover the components in FIG. 3. This is illustrative of the point that the drape is used to maintain the sterile field, but one of skill in the art will recognize that individual components shown in FIG. 3 are apt to be inside a housing and not in direct contact with the drape. One exception is the tops of the indicator lamps 328 and 332 (discussed below) which must remain visible through the drape as discussed in detail below. Also as discussed below some controls may be placed outside of the sterile field and thus located below where the drape ends on the liquid warming device.

In some implementations the user may alter a target temperature 352 for the fluid through the use of input keys 340. The target temperature 352 and the current temperature of the fluid can be displayed on a display 348. The input keys 340 and the display 348 in this illustrated implementation are placed low on the housing so that these components are below the drape 310 and outside the sterile field. In other implementations the target temperature may be set at the factory or by service personnel having access to controls or inputs within the interior of the device and not accessible to the users involved with the delivery of surgical services.

One of skill in the art will recognize that special window could be placed in the drape or the drape could be made of material with optical properties that allow a standard LED display to be read through the drape.

Thermocouple Well

One possible implementation is to use a thermocouple well 312 made of a material that conducts heat, such as metal, but is preferably made so as to have low thermal mass in order to be very responsive to changes in the temperature of the sterile fluid. Using a small diameter well and thin gauge material is useful for obtaining a low thermal mass. The thermocouple well can be a hemispheric protrusion into the sterile fluid but could also be some other shape. Preferably the thermocouple well will present a three-dimensional surface of conductive material to the sterile fluid rather than a plate of conductive material at the top of a non-conductive protrusion.

The thermocouple well may be made of the same material as the container as this will serve to decrease the cost of fabrication and eliminate the potential for leakage at the border between two dissimilar materials. A thermocouple well incorporated into a polypropylene container will afford significant responsiveness of the thermocouple in the well as the thermocouple/well combination will be extended out into the fluid.

Figure 4A:
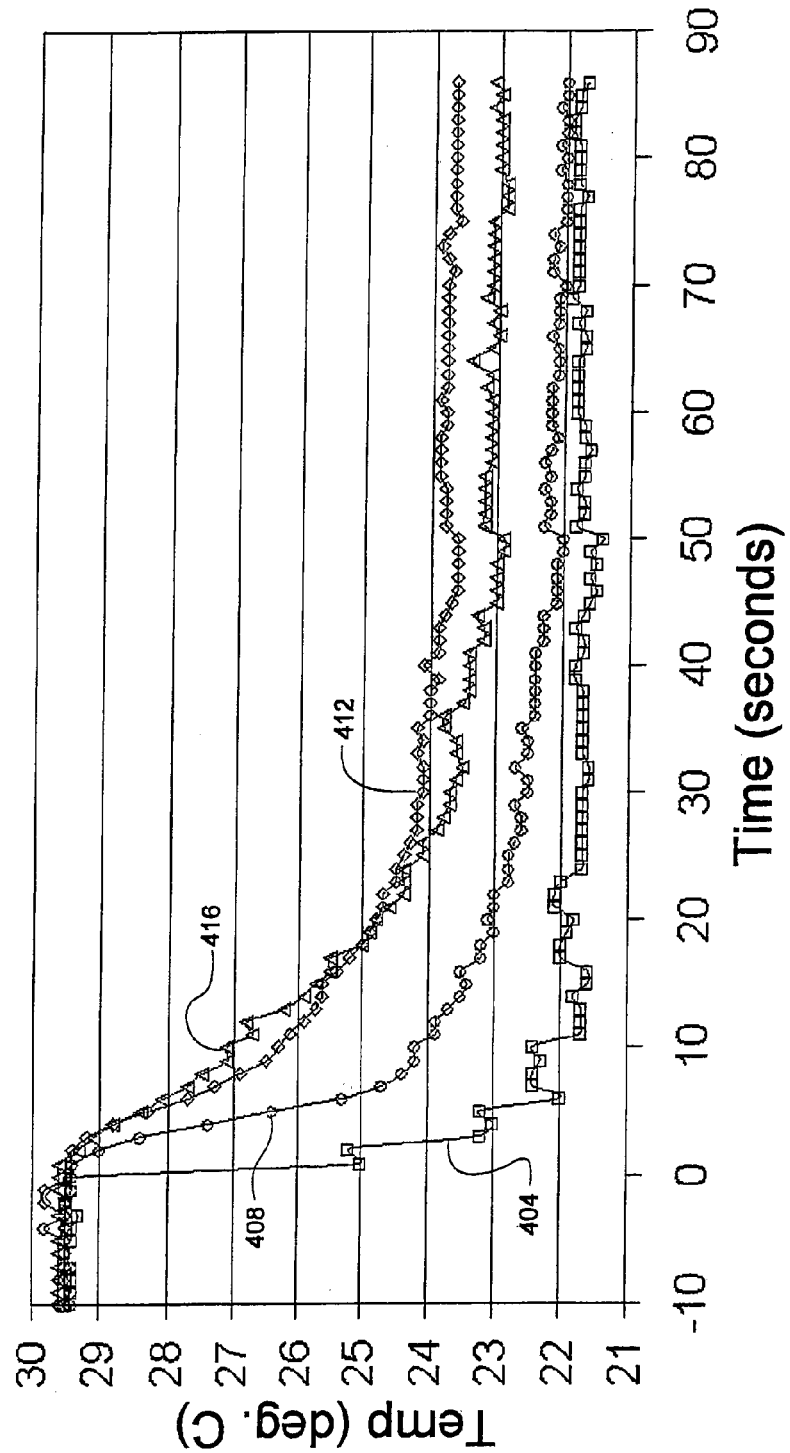

The efficacy of using a thermocouple well is illustrated in FIGS. 4A and 4B. FIGS. 4A and 4B show the responsiveness of a thermocouple placed in thermocouple well divot formed in the bottom of a six liter polypropylene basin. FIG. 4A shows the responses of four thermocouples to track the change in temperature in a basin as cold water is added. The test was done without a heater in order to focus on the ability of the thermocouples to track a change in temperature. A basin with two liters of water at 29.7 degrees Celsius had a liter of 5 degree Celsius water added (unusually cold water to make it easier to see the differences between the various measuring points). Curve 404 represents the data as measured by a thermocouple suspended in the water. Curve 404 is as expected, the most responsive to the change in temperature. Curve 408 is the curve of data as measured through a thermocouple in a thermocouple well extending into the fluid. This curve is significantly more responsive than the curves from data obtained from thermocouples placed in contact with the bottom of the basin (curve 412) or the side of the basin below the water line (curve 416). In less than a minute after the significant movement in temperature from the addition of frigid water, the temperature obtained from the thermocouple well is within a fraction of a degree Celsius of the temperature obtained from the thermocouple suspended in the fluid.

FIG. 4B shows the results when a basin with three liters of 22 degree Celsius water received an additional liter of 55 degree Celsius water. Again curve 454 for the data from the thermocouple suspended in the water is the most responsive to the change in temperature of the water. Again curve 458 for the data obtained from the thermocouple in the thermocouple well extending into the fluid is the second most responsive and quickly converges on curve 454. The curves 462 and 466 for data collected from thermocouples on the bottom and the side of the basin are again less responsive to the change in temperature. Error or bias in the thermocouples does not seem to explain the deviation of these curves from the new water temperature as the four curves were all substantially the same at the steady state before the introduction of the hot water.

Thus, using a thermocouple placed in a thermocouple well made of the same material as the basin (even relatively non-conductive material such as polypropylene) is a viable option to obtaining a responsive indication of fluid temperature without the significant problems associated with suspending a thermocouple in the fluid to be measured while trying to maintain a sterile field and not interfere with the work of the surgical staff.

A non-intuitive advantage of using such a thermocouple well rather than a thermocouple well made of a highly conductive material, such as a metal, is that the thermocouple well made of non-conductive material is less prone to being influenced by the temperature of the heat source below the container. More specifically, there is an advantage to using the relatively non-conductive plastic material for the thermocouple well in that the elevated temperature of the heat source cannot travel easily through the relatively non-conductive plastic thermocouple well to convey heat to the tip of the thermocouple.

Dual Set Points

Returning to FIG. 3, a fluid temperature sensor 316 (such as a thermocouple) is placed in thermal contact with the thermocouple well 312 and in electrical contact with a fluid temperature controller 320. The fluid temperature controller 320 varies the set point for the temperature of the heater 112 which is measured by the heater temperature detector 116. As described in more detail below the set point for the heater is not the same as the target temperature 352 for the fluid.

In order to isolate the fluid temperature controller 320 from the current used in the heater 112, a solid state relay 324 is used to translate control signals from the fluid temperature controller 320 to effectively close a switch and provide current to the heater 112.

Visual Indicators

In this illustrated implementation, two visual indicators are provided that can be seen from a distance to allow those participating in the surgery to check the fluid temperature status from afar. When the At-Temperature indicator lamp 328 is lit, this conveys that the fluid temperature is at the target temperature or within a certain tolerance of that target temperature. In contrast, when the Out-of-Range indicator lamp 332 is lit, it indicates that the liquid warming device has power and the main on/off switch 336 is turned on but the fluid is not within a certain tolerance of the target temperature. The control system may be implemented so that this light is not lit unless the limit switch (discussed below) indicates that a container is present.

In some implementations, a single Out-of-Range indicator may be sufficient as the staff would typically know whether they had added cool water or hot water to the container. In the event that the staff was not sure whether the temperature was above or below the desired range, the specific temperature could be obtained from the display 348. This gives the staff the information necessary to make an informed quantitative decision to use out-of-range fluid if the particular intended use of the out-of-range fluid would be acceptable. As noted below, one of skill in the art can appreciate that the Out-of-Range indicator could be revised to be an above range indicator and a below range indicator.

Choices for visual indicators may include using a green lamp for At-Temperature and either a red lamp or a yellow lamp for Out-of-Range. When used with the implementation described above that separates the liquid warming device from the sterile field through the use of the surgical drape 310, the indicator lights selected (size, brightness, degree of protrusion from the surface) must be suitable for providing an adequate visual signal even through the drape material which for some drapes is not fully transparent. LED lights can be suitable for at least some drape materials. Ideally the light source should be of the type that projects light towards the drape as this helps make the visual indicator visible. An alternative to having lights that can be monitored through the standard drape material is that, the lights could be made more visible by placing a window of substantially transparent material in the drape so that when appropriately placed on the fluid warming device the window is placed over the visual indicator lights.

The portion of the indicator light assembly that comes in contact with the surgical drape must operate at a temperature that can be maintained in contact with a surgical drape for an extended period of time without damaging the surgical drape. An extended period of time would mean 24 hours of contact without damaging the drape.

One could provide further detail by using separate indicator lamps for above the temperature target range and one for below the temperature target range. Perhaps, blue for too cold and red for too hot. Likewise, one could add additional indicator lamps to distinguish between close to the target temperature range but still out of range from an indication that the current fluid temperature is further from the target temperature range. For instance once could use a yellow lamp for close but not quite in range. One of skill in the art will note that flashing lights could be used to convey something different from constant lights. For example a flashing the In-Range and Out-of-Range lights might convey that the temperature is almost in-range.

Another alternative for indicator lights is to provide one light to indicate that the warming device is turned on and a second light to indicate that power is currently being applied to the heater 112. When the fluid temperature is significantly below the target temperature, the heater-on light will be lit for an extended period of time. As the temperature of the sterile fluid approaches the target temperature, the heater will be turned on and off thus causing the heater-on light to turn on and off. Contingent on the control scheme implemented to control the heater, the steady state operation of the control system to maintain the temperature of the sterile fluid 108 may be frequent switching of the heater on and off.

Optionally, the temperature of the sterile fluid can be printed along with the time or alternatively this information can be stored for printing later. In either case, a history of the temperature over time can be used in connection with other surgical records to document that the sterile fluid was at an appropriate temperature when used.

Temperature Detector Choices

A grounded thermocouple may be used for the fluid temperature sensor 316 with the benefit that the grounded thermocouple gives a fast response to changes in temperature. Ideally, the thermocouple should have a low thermal mass in keeping with the goal to have the system be responsive to changes in fluid temperatures. A RTD may be used for the heater temperature detector 116 rather than a second grounded thermocouple use of a second grounded thermocouple could lead to a ground loop. A RTD is less vulnerable than a grounded thermocouple to interference from the electro-magnetic field from the heater. Note, the use of the term "thermocouple well" is meant to convey a common name for such a protrusion and is not meant to imply that the temperature sensor must be a thermocouple.

Fluid Temperature Controller

Figure 5:
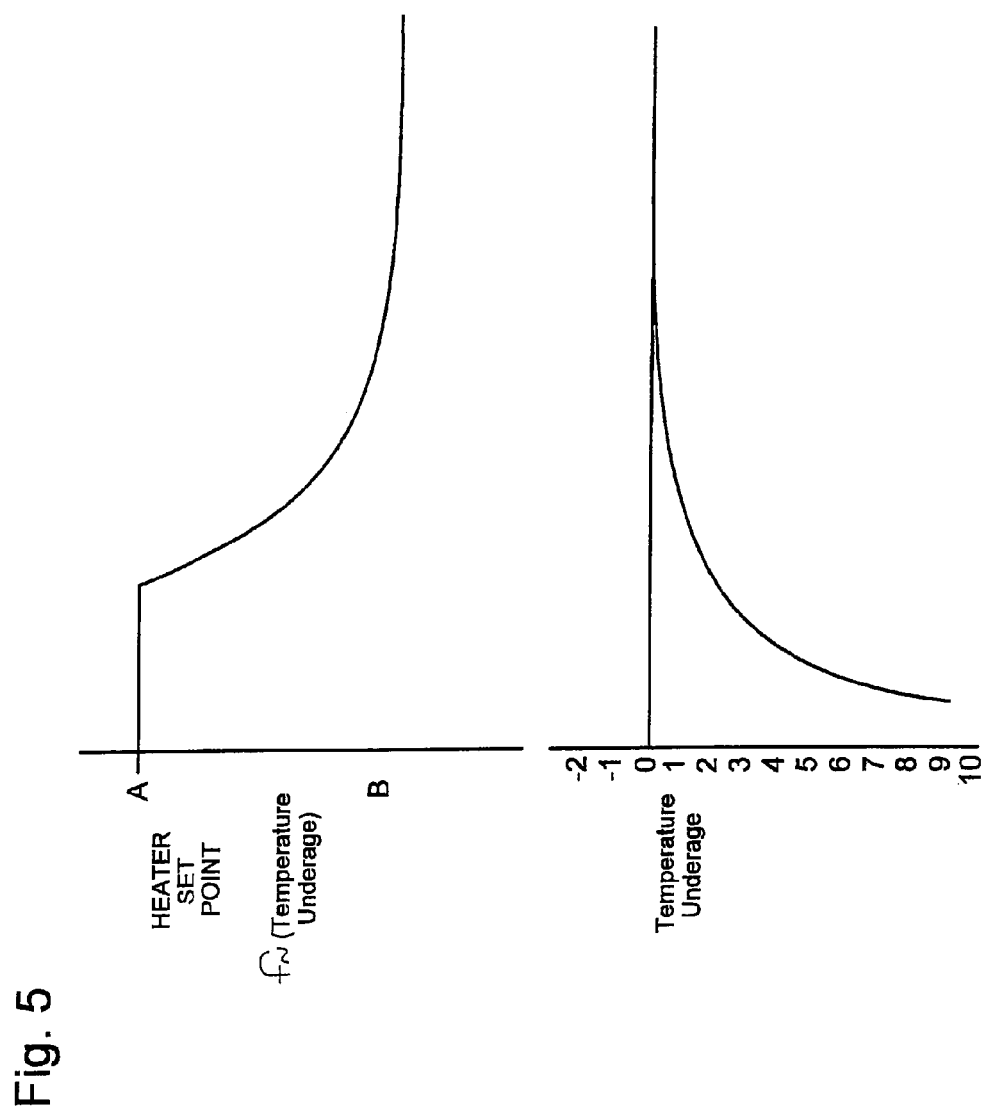
FIG. 5 shows the use of a dual-set point system to change the set point for a heater temperature based on the proximity of a measured fluid temperature to a target temperature for the fluid.

A cascade control scheme as illustrated in FIG. 5 may be used. The system responds to the current temperature underage. The temperature underage is the difference between the target temperature and the current temperature of the sterile fluid. If the target temperature is set to 100 degrees Fahrenheit then a current fluid temperature of 90 degrees Fahrenheit would indicate a 10 degree temperature underage. In some devices implementing aspects of the present invention, the target temperature can be modified by input keys 340.

The fluid temperature controller is set to operate the heater at a maximum temperature shown on FIG. 5 as temperature A. Some implementations may use a relatively high temperature in order to quickly reduce the temperature underage, but at the same time choose a temperature that is well below the temperature that would damage the removable container. For example when using a removable container made of polypropylene, a suitable conservative maximum temperature might be 180 degrees Fahrenheit. The removable container can be made of any range of suitable material such as stainless steel. The choice of container material may impact the choice of maximum temperature. At some point the tolerance to heat of the material used in the removable container may be so high as to become irrelevant that the maximum temperature is selected based on other factors such as safety of the personnel.

The steady state temperature shown as B on FIG. 5 is not a programmed number but is the temperature of the heater that maintains the sterile fluid at the desired target temperature. The temperature needed to maintain the fluid at 100 degrees Fahrenheit will be slightly higher in an operating suite with a lower ambient air temperature than in a similarly situated operating suite with a higher ambient air temperature. The maximum temperature may be used as the set point for the heater until the temperature of the sterile fluid is relatively close to the target temperature. For example, the maximum temperature may be used until the temperature underage is only 2 degrees Fahrenheit.

As the temperature of the sterile fluid approaches the target temperature, the set point for the heater is reduced thus slowing the rate of temperature increase of the sterile fluid. A suitable means for controlling the heater set point is the use of a standard PID (Proportional Integral Derivative) controller. An example of a suitable PID controller is a Series 988 Controller manufactured by Watlow of Winona, Minn., www.waflow.com/products/controllers.

As the controller seeks to reduce the output of the heater, the controller operates the relay to reduce the percentage of time that the heater receives power. Thus, a heater maintaining fluids at the desired fluid temperature would be provided with power a smaller percentage of the time compared with the same heater bringing the same volume of fluid to the desired temperature as the latter is operating at a higher set point temperature and the below temperature volume of fluid absorbs heat more readily.

An alternative implementation would remove the ability of the user to adjust the target temperature and would essentially have a fixed target temperature. In such a case, the heater set point would become a function of the sterile fluid temperature as there would be a consistent relationship between sterile fluid temperature and the temperature underage.

Based on the data sets discussed in connection with FIG. 4A and FIG. 4B, the use of a container with the temperature sensor placed below the container or outside a wall of the container would tend to be less responsive to the changes in fluid temperature than a temperature sensor placed in thermocouple well. When setting a controller for such a system, it may be necessary to stop operating the heater at the fixed elevated set point (see A on FIG. 5) at a larger underage value so that the combination of the lagging response of a temperature sensor placed below the container and the elevated heater set point do not drive the temperature of the heated sterile fluid above the desired target temperature. Conversely, the use of a thermocouple well for the temperature sensor to provide a more representative temperature to the controller allows the use of the elevated heater temperature longer and thus shortens the time needed to bring a cooled container of fluid to the target temperatures.

Limit Switch

Figure 6:
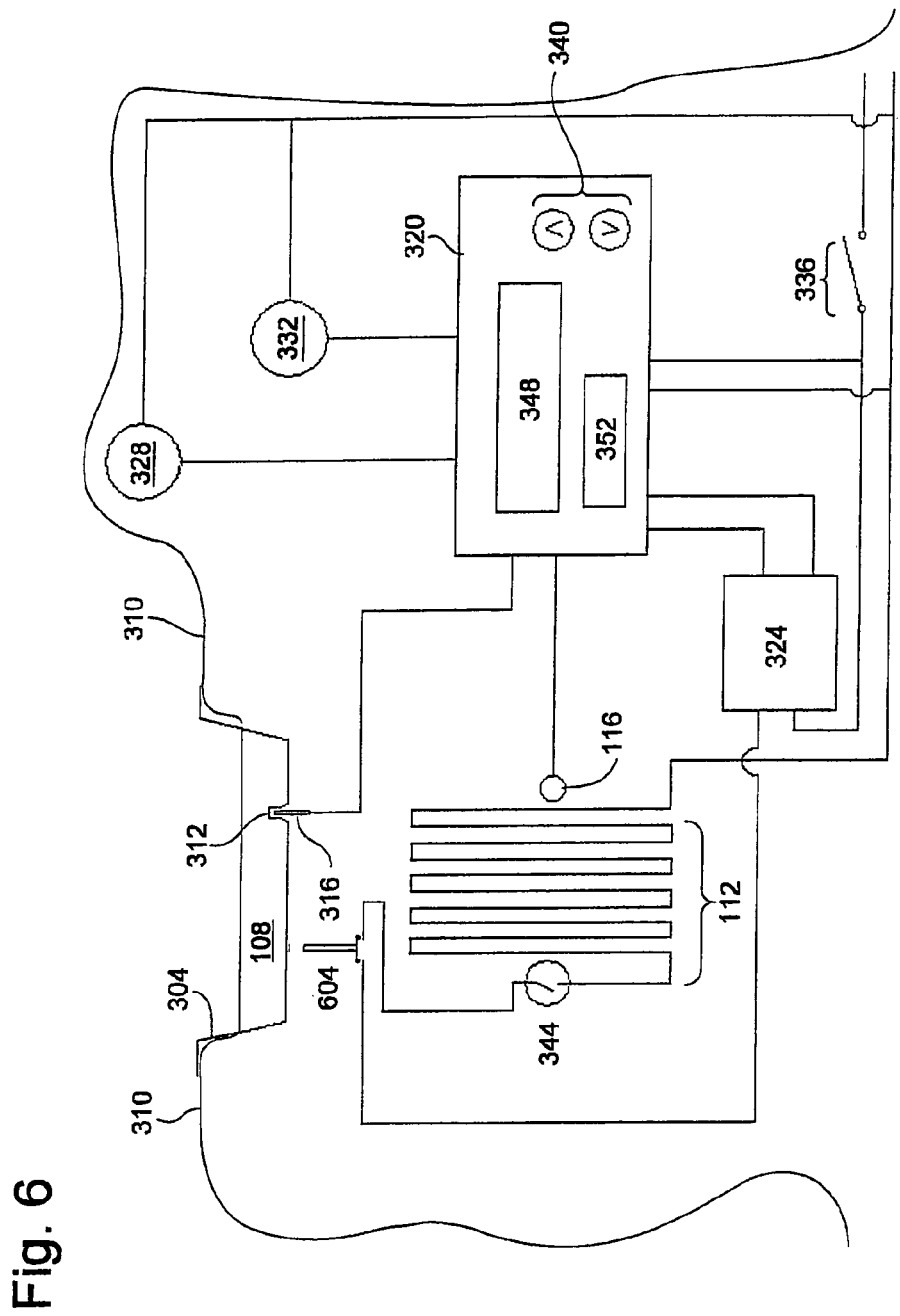
FIG. 6 shows another implementation of the present invention that modified the implementation in FIG. 3 to add a limit switch 604.
Figure 7:
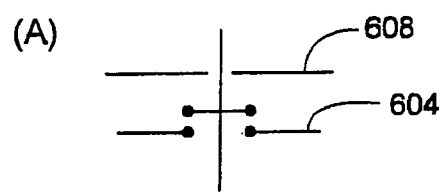
FIG. 7 which includes drawings (A), (B), (C) and (D) provide a more detailed explanation of the interaction of the limit switch 604 with various basins.
Figure 7:
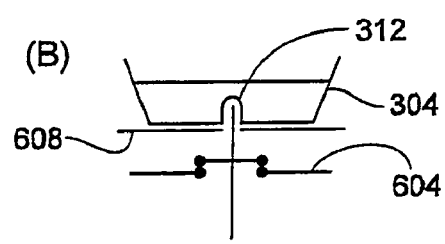
Figure 7:
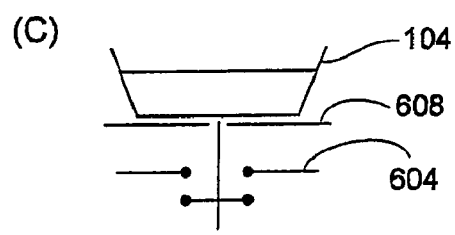
Figure 7:
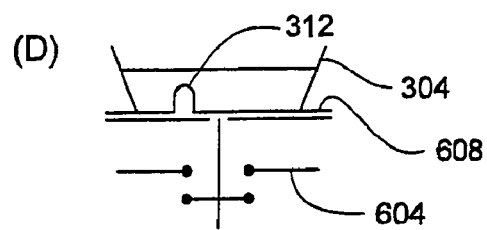

A modification of FIG. 3 is shown in FIGS. 6 and 7. A container limit switch 604 is added to prevent power from reaching the heater 112 unless it is appropriate to allow the heater to get hot. The container limit switch 604 may be implemented to detect two conditions. The first condition is the absence of a removable container. The second condition is the use of a container without a corresponding well as this container may not be able to tolerate the application of heat at maximum temperature A as temperature A is chosen based on a specific container material. A careful observer will note that while FIG. 6 depicts limit switch 604 as a limit switch and as a reminder places the limit switch near the container 304, it does not show the interaction between the limit switch and the temperature sensor or the thermocouple well. As this is primarily a control system drawing, FIG. 6 does not show the mechanical interaction between the limit switch 604 and the temperature sensor's insertion in the thermocouple well 312 as this is better conveyed by other drawings and text.

FIG. 7 illustrates the various cases. In FIG. 7A, the thermocouple protrudes up through the heater plate surface 608 but does not contact anything at all. This causes the limit switch activated by the amount of extension of the thermocouple to ride high and fail to close the container limit switch 604.

FIG. 7B illustrates the thermocouple rising through the heater plate surface 608 and contacting the top of a thermocouple well 312 in a container 304. In FIG. 7B the limit switch 604 is closed and current can pass to the heater to heat the sterile fluid.

FIG. 7C illustrates a basin 104 without a corresponding thermocouple well in the appropriate location. The bottom of the basin 104 pushes the thermocouple down to the extent that the limit switch is opened and no current is provided to the heater. This prevents the heater from applying a maximum temperature that is beyond what the unknown container can withstand. The operation of the limit switch 604 as shown in FIG. 7A or 7C could prevent the application of heat to supplies placed in the fluid heating device that are not intended to be heated. While it is not suggested that the fluid heating device be used to carry supplies in this way, a limit switch with an over-travel position that is open is less likely to inadvertently allow heat to be applied to something other than a container with an appropriate thermocouple well.

FIG. 7D is another case of the thermocouple being depressed too far and thus opening the container limit switch. In FIG. 7(d) the thermocouple well 312 is not properly aligned with the thermocouple. Continuing to operate with the container in a misaligned position is apt to be sub-optimal as the thermocouple will not receive the current fluid temperature and may be partially isolated from the actual temperature. Optionally, the warming container controls provide an indication (such as another indicator lamp) whenever the removable container is pushing the limit switch open (over-travel) so that an operator can detect and correct the problem.

One of skill in the art will recognize that the illustrations in FIG. 7 convey the concepts and situations addressed by the limit switch and are not necessarily representative of the specific arrangement of the limit switch itself. For example, the limit switch could be implemented with a spring loaded horizontal component that moves in and out as a vertical piece of varying width moves up and down.

Figure 8A:
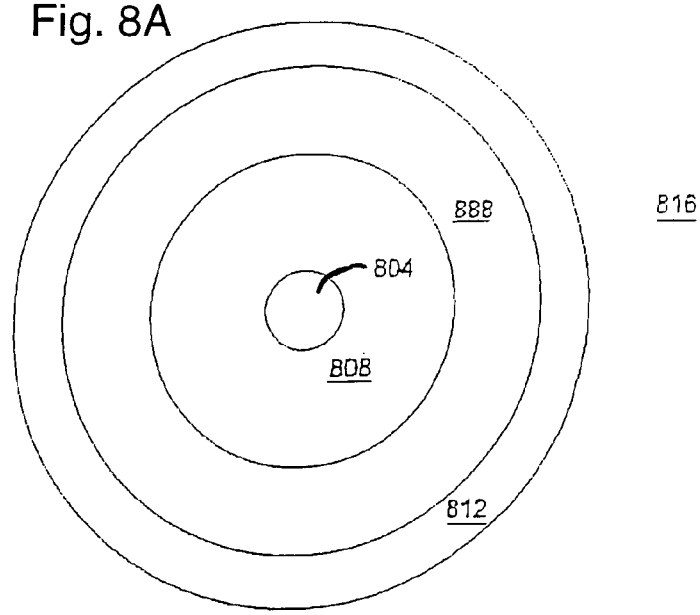
FIGS. 8A, 8B and 8C provide details of one implementation of the present invention where the basin 850 with integrated thermocouple well 854 pushes down on the limit switch actuator 808 when the temperature sensor 804 is inserted into the thermocouple well 854 by placement of the basin 850.

An alternative implementation of the limit switch of FIG. 7 is illustrated in FIG. 8. FIG. 8A is a view from the top of the temperature sensor 804 surrounded by limit switch actuator 808, limit switch guide 888, insulating zone 812, and conductive material 816. The conductive material conveys heat from the heater below the conductive material to the bottom of the container.

In this implementation the temperature sensor 804 is substantially isolated form the temperature of the conductive material 816 by the limit switch guide 888 and the insulating zone 812. The limit switch actuator 808 may also serve as a thermal insulator to help isolate the temperature sensor 804 from the conducting material 816. Placement of limit switch actuator 808 surrounding the temperature sensor 804 helps protect the temperature sensor 804 when the container is not in the cavity of the liquid warming device and staff may be tempted to place items in the cavity. While the limit switch actuator and limit switch could be placed away from the temperature sensor, it is preferable to have the limit switch actuator near the temperature sensor as this minimized the number of places that have components that stick through the layer containing the resistive heater. By minimizing the number of places where the resistive heater is not present, the design provides for more rapid and uniform heating of the liquid through the container.

Figure 8B:
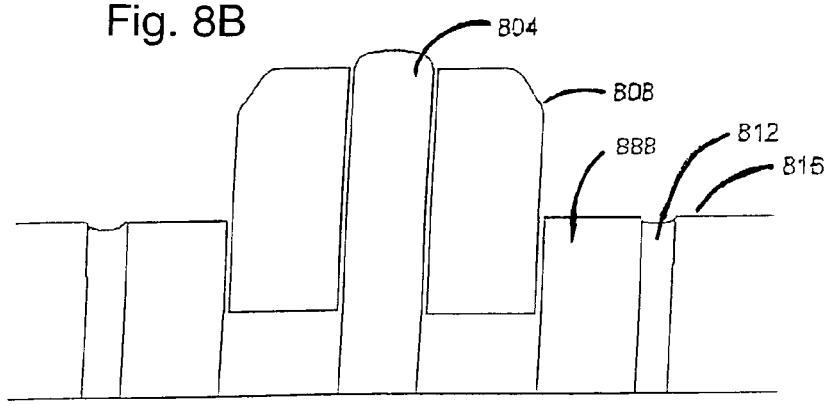

FIG. 8B is a side view of the components shown in FIG. 8A. From the side, one can see the temperature sensor 804 protruding from the extended limit switch actuator 808. FIG. 8B also shows the relative position of the limit switch guide 888, the insulating zone 812 and the start of the conductive material 816.

Figure 8C:
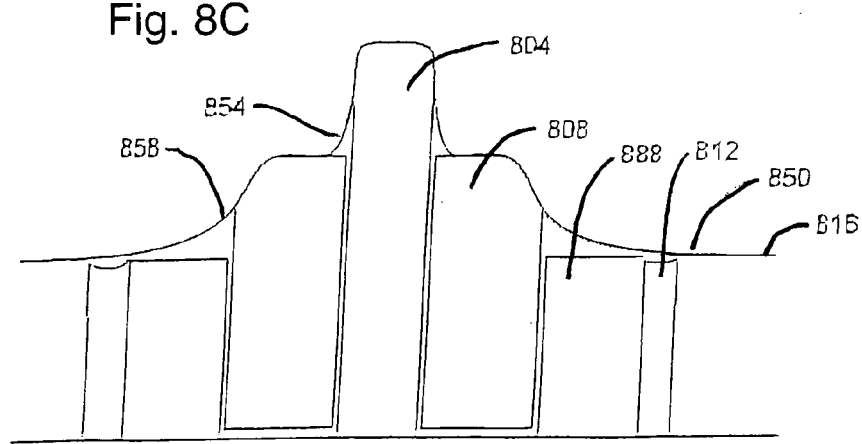

FIG. 8C shows a partial cut-away view of a container 850 with integrated thermocouple well 854. When the container 850 is placed to align the thermocouple well 854 above the temperature sensor 804, the container 850 pushes down on the limit switch actuator 808 which moves downward relative to the temperature sensor 804, limit switch guide 888, insulating zone 812, and conductive material 816. Movement of the limit switch actuator 808 within a prescribed amount activates a limit switch that indicates that an appropriate container is in place. As described above, over-travel of the limit switch indicator may be used to deactivate the limit switch. In this implementation with the protruding temperature sensor, over-travel would not occur from use of a container without a thermocouple well 854 as such a container (not shown) would be prevented by the fixed protruding temperature sensor 804 from depressing the limit switch actuator 808. Over-travel would be rare in this configuration but might indicate that someone has placed something heavy adjacent to the temperature sensor 804 to intentionally or possibly unintentionally depress the limit switch actuator 808.

Examples of suitable materials for the components in FIG. 8 are as follows. The limit switch actuator can be made of Nylon or Delrin as they have low friction and low thermal conductivity. The limit switch guide can be made of polytetrafluoroethylene (PTFE) (commonly known by the registered trademark Teflon). PTFE is resistant to heat and is slippery which works well for the need for the limit switch actuator to move relative to other components. The insulating zone can be made of a silicone which helps seal the system and like PTFE has a high service temperature. A suitable material for this conductive material 816 is an aluminum plate that is 0.032 inches thick. While thicker plates would work, it is a design goal to have minimal thermal mass where possible to make the system responsive.

A number of means can be used to assist the surgical staff in positioning the removable container so that the thermocouple well is aligned with the thermocouple. For example, providing an alignment line on the removable container and a corresponding line on the liquid warming device. As the container is apt to be used with a drape, the alignment line on the liquid warming device would preferably be a light that could be seen through the drape.

Optionally, the placement of the thermocouple well on the container could be used as a way to ensure that the proper container from a set of possible container is being used with a particular warming device. This would be appropriate if it was important to prevent one removable container with a thermocouple well from being used in the wrong liquid warming device. For example the different device/container pairs could place the temperature sensing device and corresponding thermocouple well different radial distances from the center of the container. Another way of preventing the wrong type of removable container from being used in a particular liquid warming device is to use thermocouple wells of different depths in the different removable container products. By adjusting the limit switch to require an interaction between the thermocouple and a thermocouple well of a certain depth, the thermocouple well depth can be used to limit the viable choice to a single removable container product and thus prevent the inadvertent use of wrong removable container product in the liquid warming device.

A simple way of aligning the thermocouple well with the thermocouple is to place both so that they meet in the center of the removable container. Such an implementation would need to rely on other attributes in order to prevent an inappropriate container/device pairing.

An alternative to relying on the thermocouple/thermocouple well interaction to ensure that an appropriate removable container is inserted in the fluid heating device is to provide the removable container with an RF ID tag (Radio Frequency Identification tag) and providing a sensor in the liquid warming device. The RF ID tag would be useful whether or not the limit switch tested for an appropriate reaction between the thermocouple and the thermocouple well as it would make it more difficult for a manufacturing entity to sell counterfeit removable containers of inferior quality.

Protection Against Heating Empty Containers

An alternative implementation would make the limit switch spring loaded so that a container with an appropriate thermocouple well placed in the proper position would still not enable the limit switch as shown in FIG. 7(B). This alternative implementation would require the application of more weight than is provided by an empty container of a known material. In order to enable the limit switch, an additional force, presumably from additional weight from fluid in the container, would need to be applied. While this additional force could be provided by a gloved thumb of a person in the operating room or a solid object placed in the removable container, the goal would be to decrease the likelihood that the liquid warming device is applying heat to a removable container without a substantial amount of fluid. It may be prudent to add an audible or visual alarm to indicate that the liquid warming device is currently not maintaining the sterile fluid at the target temperature as the liquid warming device believes that there is either an improper removable container or an insufficient amount (weight) of sterile fluid. The use of an alarm will prevent the surgical staff from missing that the fluid heating device is not maintaining the sterile fluid at temperature for use in the surgical procedure.

As the temperature of the heater will normally be selected to be well below the melting temperature of the container material, it will not normally be necessary to make the limit switch sensitive to the weight or lack of weight of fluid in the container. But this would not address the situation of a container that becomes empty or nearly empty as the fluid is used during surgery.

One of skill in the art could impose other forms of protection against heating an empty container such as requiring a user to confirm that an appropriate sterile container and an adequate level of fluid are present by a response to a question posed by the controls during the power-up sequence for the fluid heating device. It is recognized that asking for confirmation of fluid in the container at the start of the process does not address the situation of a container becoming empty during the surgery and left while empty or nearly empty in the fluid warming device.

A co-pending application is for a Heating Element for Liquid Warming Device with U.S. Ser. No. 11/209,430. The warming pad disclosed in that application can be advantageously used with the present application with the modification that the warming pad be provided with an opening that runs through the warming pad so that the control system of the liquid warming device can make contact with the thermocouple well in the bottom of the modified container. The warming pad described in the above-referenced application provides improved thermal contact to the irregularly shaped container bottom, a heat distribution layer to reduce the differences in temperature across the heating pad surface, and a low thermal mass to improve responsiveness of the warming pad.

As the teachings of the present application could be applied to liquid warming devices using other types of heating systems, these applications have been filed separately in order to make clear that the details disclosed in one application should not be misinterpreted as limitations of the disclosed invention in the other application.

An alternative heating system would use trace wire resistive heating embedded in silicon to convey heat to a low thermal mass plate (such as described in connection with element 816 below) to convey heat to a relatively flat bottomed container. The heater would typically place the heater temperature detector 116 and the mechanical thermostat 344 in the center of the heater (below the approximate center of the container). Typically, the resistive trace heater would not run through this center zone with the two measurement components.

Characteristics of Thermocouple Well and Interaction with Temperature Sensor

One characteristic of the container thermocouple well 854 discussed above is that the edge 858 of the thermocouple well be adapted to depress the limit switch actuator 808 in order to provide sufficient movement of the limit switch actuator 808. In the event of a limit switch actuator 808 connected to a limit switch sensitive to over-travel, then the shape of the edge 858 of the thermocouple well and the shape of the limit switch actuator 808 need to be coordinated so that the presence of an appropriate container provide the appropriate depression of the limit switch actuator 808.

One of skill in the art will recognize that the use of a thermocouple well that lacks the edge 858 of the well but instead goes from the portion of the thermocouple well adapted to receive the temperature sensor to the flat bottom of the container would tend to interact with a limit switch actuator by driving the actuator close to flush with the conductive material 816. Over-travel would be extremely rare if the limit switch was adjusted to close when the top of the actuator is flush. Similarly one could have a ring or other shape around the thermocouple well that projects downward so that the container projection would depress the limit switch actuator below the level of the conductive material 816. Likewise the interaction between the container and the limit switch actuator 808 does not have to be an interaction that encircles the temperature sensor 804 as shown in FIG. 8.

Another characteristic of a thermocouple well 854 discussed above is that the thermocouple well be made of the same material as the container 850. As discussed above, the useful attribute of having the thermocouple well being a good thermal conductor to convey changes in fluid temperature through the thermocouple well to the temperature sensor is deemed less important than isolating the temperature sensor 804 from the heater so that the temperature sensor is not unduly influenced by the temperature of the heater and heat plate rather than the temperature of the fluid. Thus, in this application it is preferably to use a material that is not a good thermal conductor so that heat sensed by temperature sensor 804 is substantially the temperature of the fluid in the container that surrounds the elevated end of the temperature sensor with minimal impact from thermal energy traveling from the conductive material 816 into the wall of the container 850 and through the thermocouple well 854 to the tip of the temperature sensor 804.

Another characteristic desirable in a thermocouple well 854 is essentially an interference match between the height of a protruding temperature sensor 804 and the corresponding height of the cavity in the thermocouple well 854 so that a container thermocouple well 854 appropriately positioned on a temperature sensor 804 will abut against the top of the temperature sensor 804. To the extent that manufacturing tolerances cannot be fully controlled, it is better for the thermocouple well 854 to be slightly deeper and thus have a small gap above the temperature sensor than to be too shallow and cause the container to fail to make good contact with the conductive material 816 and effectively depress the limit switch actuator 808.

Another characteristic desirable in a thermocouple well 854 is essentially an interference fit between the sides of the temperature sensor 804 and the corresponding portion of the thermocouple well 854. Failure to get a close fit between the walls of the temperature sensor and the thermocouple well may lead to limited contact between the temperature sensor and the thermocouple. While relying nearly exclusively between the contact from the very top of the temperature sensor 804 and the corresponding portion of the thermocouple well 854 would be operative, the small amount of thermal contact relative to the thermal mass of the temperature sensor 804 would tend to decrease the responsiveness of the system to changes in fluid temperature.

One of skill in the art could arrange for an interference fit in a number of ways including ways that expand the thermocouple well to provide the interference fit and ways that compress or otherwise decrease the cross section of the temperature sensor 804. An illustrative example should be sufficient to illustrate the point (discussed in connection with FIG. 9).

Another characteristic desirable in a thermocouple well 854 is the ability to insert the temperature sensor 804 into the thermocouple well without compressing the air present in the empty thermocouple well 854 or forming a vacuum when the container is lifted off of the temperature sensor 804. Compressing air when placing the container on the temperature sensor 804 may impede seating the thermocouple well so that it pushes down on the limit switch actuator 808 sufficiently to enable the limit switch 604. Trapping and compressing air may inadvertently add an insulating layer between the top of the temperature sensor 804 and the corresponding section of the thermocouple well 854 and thus decrease the responsiveness of the temperature sensor 804 to changes in the temperature of fluid. A combination of a temperature sensor 804 and a thermocouple well 854 that forms a vacuum when the container is removed at a normal speed from the warming device would temporarily resist the upward movement of the container and then let go as the vacuum ceases to operate once the container has moved a sufficient amount. In an extreme case this could lead to splashing of the sterile fluid out of the container when a vacuum is formed and extinguished. In most cases it would not lead to splashing but it would be viewed as an undesirable quirk.

One way to prevent both the compression of air in the thermocouple well and the temporary formation of a vacuum during removal of the container is to add one or more air vents to the thermocouple well. Another way is to select a temperature sensor shape that would not lend itself to compressing air or forming a vacuum. For example, the use of a sloped shape to the temperature sensor such as a frustum, truncated pyramid, hemisphere, or other analogous shape and a corresponding thermocouple well is much less likely to be a problem than a cylindrical temperature sensor inserted into a corresponding cylindrical bore in the thermocouple well.

FIG. 9 shows an example of a suitable thermocouple well in accordance with the characteristics discussed above. This example is meant to illustrate the concepts of a desirable design and is not to scale. FIG. 9A shows a thermocouple well 904 as looking up from the temperature sensor to the bottom of the container just before the thermocouple well comes into contact with the protruding tip of the temperature sensor. The gap between opposing walls 908 and 912 for the thermocouple well is length D1 for a thermocouple well 904 before insertion of temperature sensor 804. In this example the tip of the temperature sensor is cylindrical with rounded shoulders but having a diameter of more than D1 below the shoulders. Thus, when the tip of the temperature sensor is inserted into thermocouple well 904, the opposing walls 908 and 912 are forced apart to approximately D2, the minimum amount necessary for the temperature sensor 804 to be inserted into the thermocouple well 904. This will lead to a substantially conforming interference fit between the walls of the thermocouple well 904 and the temperature sensor 804 which promotes better tracking of the temperature of the fluid on the other side of the thermocouple well walls.

Well wings 916 and 920 serve two purposes. First, they serve as hinges to allow the flexing of walls 908 and 912 to allow for the interference fit described above. Second the wings help to vent the thermocouple well as the temperature sensor 804 is inserted and removed from the thermocouple well to reduce the tendency to either compress air or to form a vacuum. The shape of the thermocouple well is apt to leave some small amount of gap 928 above the well wings 916 and 920 as the conforming fit will run between the well wings but be less conforming at and above the well wings.

Figure 10A:
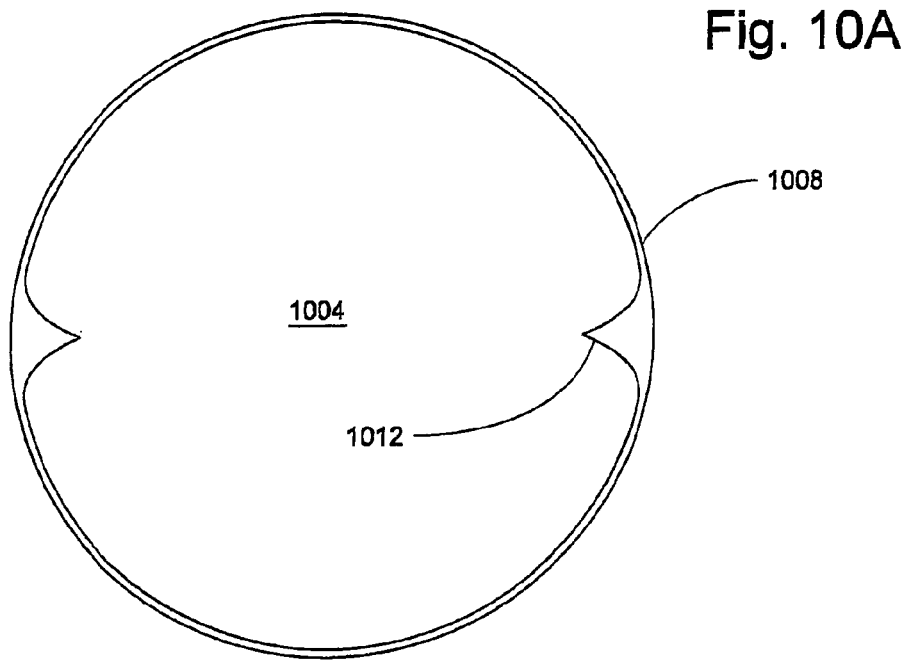
FIGS. 10A and 10B illustrate possible alternative implementations that provide for venting of air out of and into a thermocouple well (1008 or 1058) as the temperature sensor (1004 or 1054) is inserted and removed.
Figure 10B:
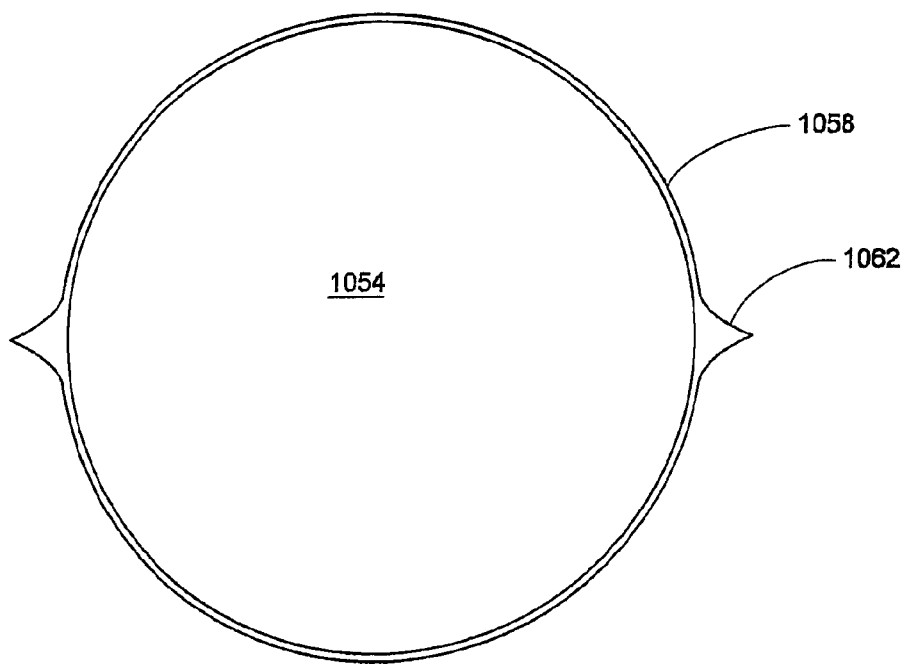

FIG. 10A illustrates that a substantially conforming fit could be obtained by having manufacturing tolerances so that the temperature sensor 1004 has essentially the same shape as the distal tip of the thermocouple well 1008 except for a vent ridge 1012 in the temperature sensor 1004 housing to allow for air to vent out or in during the insertion or removal of the temperature sensor 1004. FIG. 10B is similar except that the vent ridge 1062 is part of the distal tip of the thermocouple well 1058 and the temperature sensor 1054 does not have a vent ridge. (In order to facilitate identifying the various components, the gaps between the temperature sensors and the thermocouple walls are enhanced in FIG. 10).

Another example of a temperature sensor thermocouple well pairing designed to provide a substantially conforming fit is an exterior sheathe connected to the temperature sensor and made of a highly conductive material but is wrapped around the temperature sensor as a helical compression spring that will compress as needed to fit inside the thermocouple well but will expand to make contact with the inside wall of the thermocouple well.

Another example of a pairing designed to provide a substantially conforming fit is to attach the temperature sensor to a thermally conductive sleeve that is an expanding collet-like piece that moves with the limit switch actuator. As the tip of the collet is narrower than the tip of the temperature sensor, when the collet moves downward with the limit switch actuator as the container moves downward, the temperature sensor tip will be forced into the tip of the collet causing the collet fingers to spread apart and make contact with the thermocouple well wall.

In a variation analogous to that shown in FIG. 10B, the thermocouple well for use with a cylindrical temperature sensor could be slightly elongated in one direction so that the slightly oval thermocouple well would flex to receive the cylindrical temperature sensor and the two end points along the long axis of the oval thermocouple well would serve as vents.

The thermocouple well for use with an essentially cylindrical distal end of a temperature sensor could be a polygon such as a hexagon or octagon that would receive the cylindrical temperature sensor but would have a set of small vents along the corners of the polygon.

These examples just illustrate the range of ways that one of skill in the art can implement this particular teaching of the present invention.

Alternative Control System and Alternative Heaters

The dual set point control system illustrated in FIGS. 3 and 6 may be implemented in conjunction with conventional strip heat technology to provide the heat to the conductive material 816 that is in thermal contact with the container bottom to heat the fluid 108.

Figure 11:
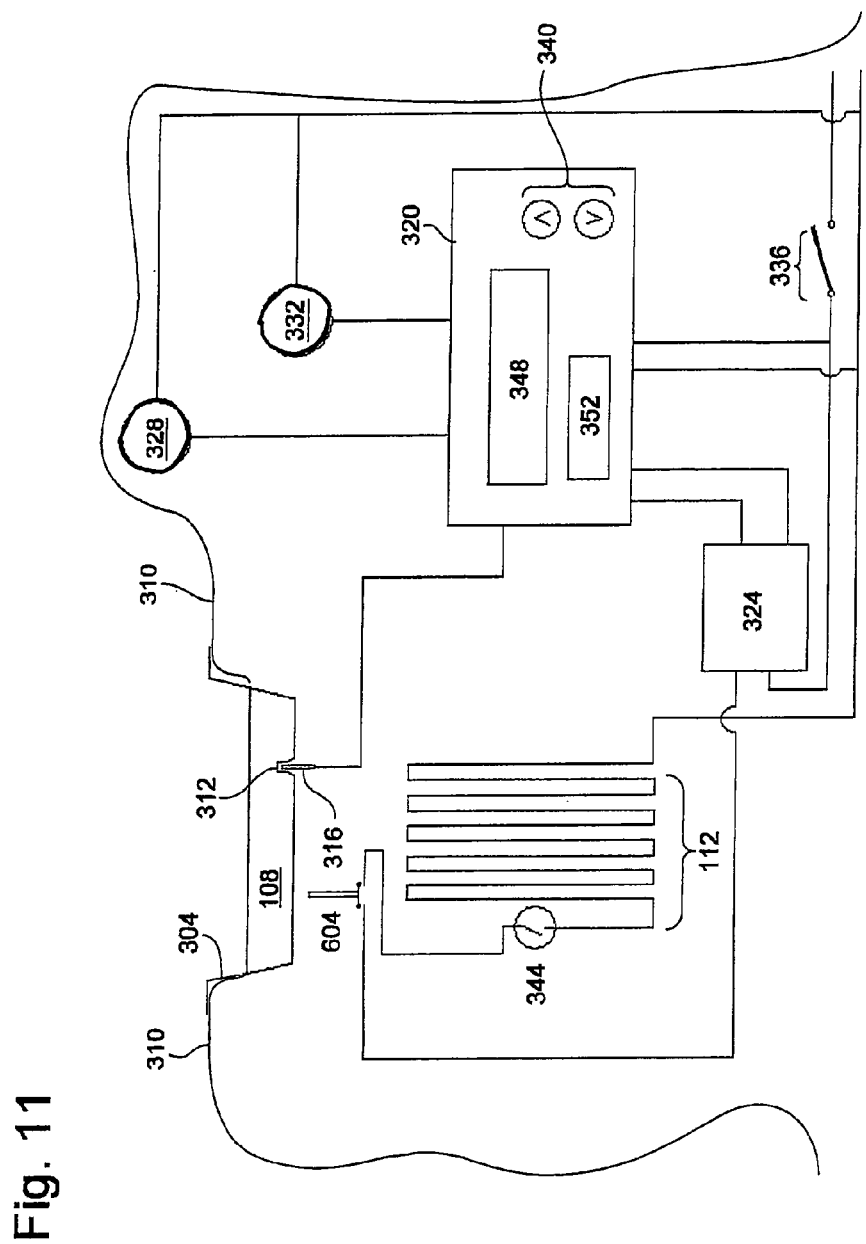
FIG. 11 illustrates a control system using a single set point rather than a dual set point as the implementation in FIG. 11 does not monitor the temperature of the heater 112.

A control system that delivers energy to a heater based solely on the temperature of the fluid is possible and is part of an alternative implementation of the present invention. An example of a control system adapted for operation based solely on the temperature of the sterile fluid is shown in FIG. 11. The most striking difference between FIG. 11 and FIG. 6 is that FIG. 11 lacks the heater temperature detector 116 found in FIGS. 6 and 3. Controller 320 attempts to regulate heater 112 through relay 324 to provide suitable thermal input to heat fluid 108 to target temperature 352 as measured by temperature sensor 316 through thermocouple well 312.

In this implementation great care would need to be exercised when heating fluid 108 in a plastic container 304 to ensure that the local temperature of the heated container could never exceed the safe operating temperatures of the plastic container. For instance, if cold water were poured in the container 304, the controller 320 would detect the large temperature underage and call for the addition of heat by having relay 324 provide current to heater 112. Since there is a lag between heater temperature (now unmeasured) and fluid temperature as sensed by temperature sensor 316, the sensor 316 would continue to detect a temperature underage for a long time and the controller 320 would have no way of determining if it could call for additional heat input without causing the heater 112 to drive the plastic container bottom above safe limits. In this scenario the heater capacity would need to be reduced so if the heater were on at 100%, the temperature would never exceed the plastic container safe operation temperature. By monitoring the heater temperature in addition to the fluid temperature, the heater capacity can be larger so that additional heat input can be delivered when needed without compromising the plastic container.

A control system that does not attempt to measure the temperature of the heater could be used with heaters beyond the resistive heater ("strip heater") discussed above. For example, a system using an infrared heating source to heat the fluid, perhaps from above could be operated using the control system set forth in FIG. 11. Note that the drape 310 would need to be selected and placed relative to the heat source so that the drape is not prone to damage from heat as infra-red heat sources are often extremely hot.

Those of skill in the art will recognize that other heating sources such as microwave, ultrasonic, and induction heating could be used with the control system in FIG. 11 and other teachings of the present invention.

Example of a Suitable Large Container

Figure 12:
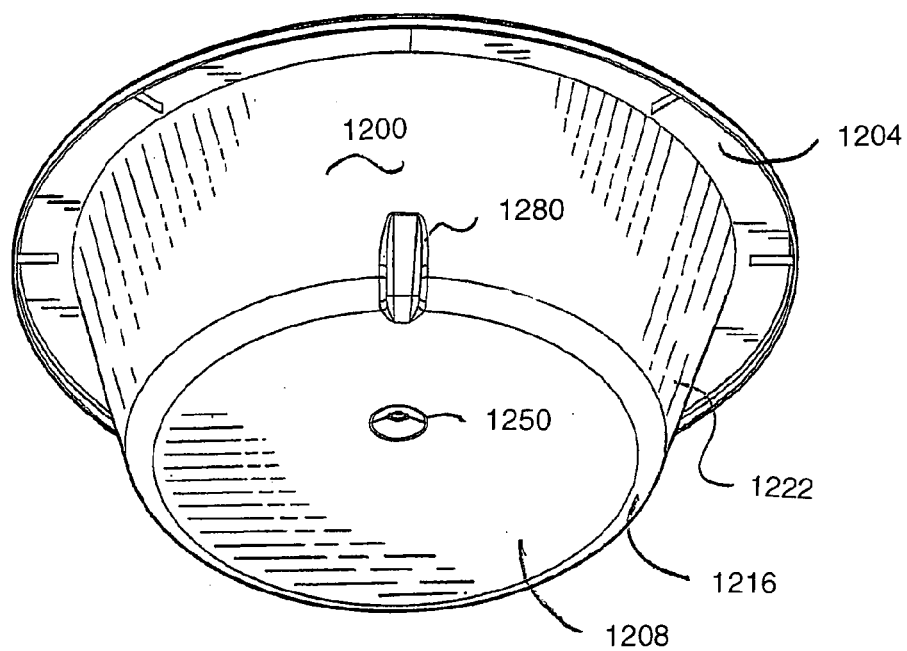
FIGS. 12 through 18 show various views a basin that may be used with certain implementations of the present invention as this basin has a thermocouple well 1250 and an alignment channel 1280.

FIGS. 12 through 18 illustrate a basin 1200 that can be used in accordance with the present invention. This basin would be used to substantially fill the cavity in the top surface of the liquid warming device. FIG. 12 shows a bottom and side perspective view of basin 1200 with rim 1204, bottom 1208, sidewall 1222, and sloped ring 1216. Thermocouple well 1250 is partially visible. An optional alignment channel 1280 is present at the intersection of the bottom 1208 and a portion of the sidewall 1222. This alignment channel 1280 fits over a corresponding ridge in the fluid warming device (not shown) to provide an aid in aligning the basin 1200 relative to the fluid warming device so that the temperature sensor can be forced into the interference fit in the thermocouple well 1250. (Note that one of skill in the art can appreciate that an alignment channel would be of value even if the thermocouple well does not require the exertion of force for an interference fit.)

Figure 13:
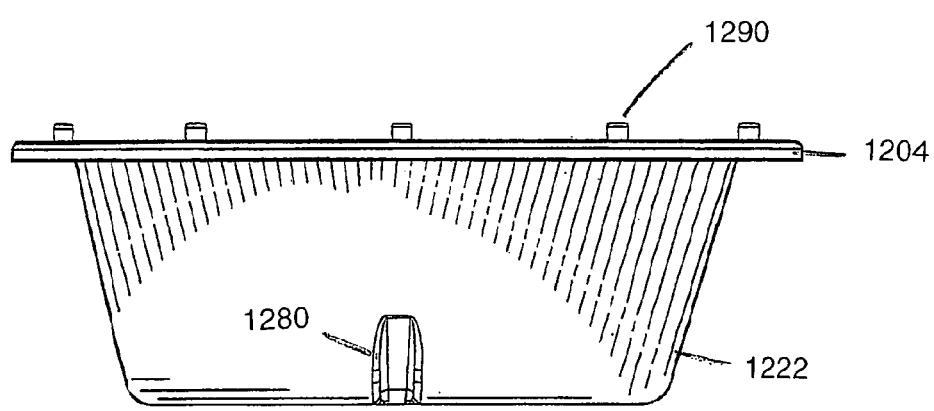

FIG. 13 provides a side plan view of the same basin 1200 with the alignment channel 1280 visible. FIG. 13 includes optional rim protrusions 1290 that protrude upward from the top face of the rim 1204. As the rim protrusions may be formed so as to be hollow, the rim protrusions 1290 may be used as an alternative or a compliment to the alignment ridge 1280 to position the container in a particular orientation. This would require an interaction with corresponding protrusions from the top surface of the liquid warming device or from an adapter (discussed below). If the alignment is to be controlled primarily or exclusively by alignment of the rim protrusions 1290 and the corresponding protrusions on the liquid warming device or adapter (discussed below), then it may be advantageous to have an asymmetric pattern of rim protrusions 1290 so that there is only one rotational position that aligns all the rim protrusions 1290 with the corresponding protrusions.

The interaction between protrusions on the liquid warming device (or on an adapter) and a set of rim protrusions may be of benefit even if the liquid warming device relies on an alignment ridge to for alignment of the container as the protrusions and hollow rim protrusions 1290 may be sized for an interference fit or to engage a drape so that the protrusions plus the drape form an interference fit with the rim protrusions to help maintain the position of the container during use and to help maintain the boundary of the sterile field.

Figure 14:
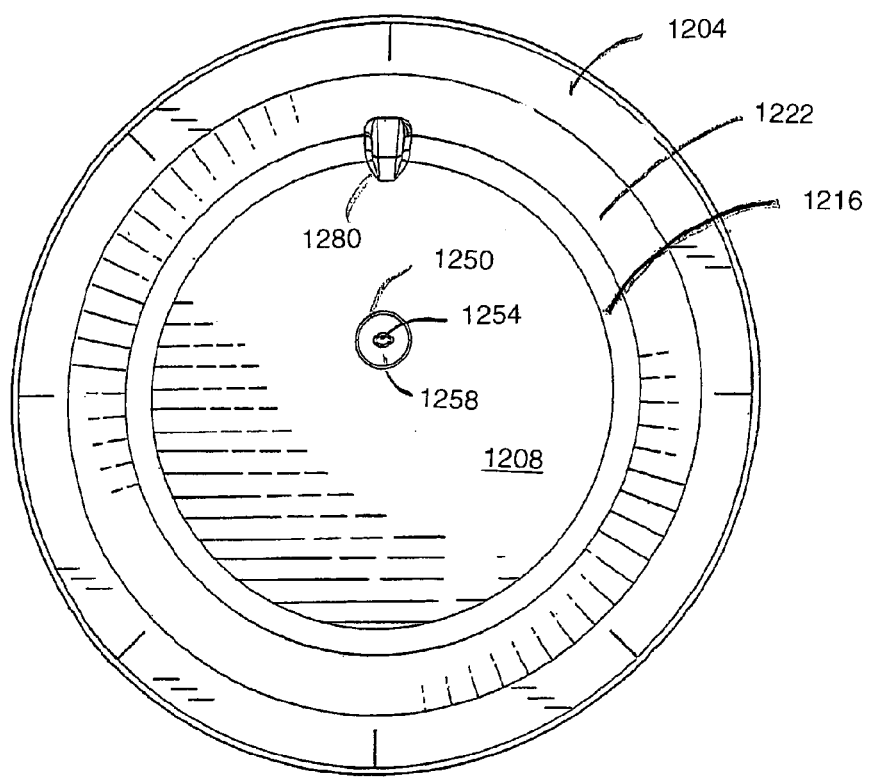

FIG. 14 is a bottom plan view that shows that the center of the thermocouple well 1250 is a winged divot 1254 along the lines discussed in connection with FIG. 9. The winged divot 1254 is surrounded by an indentation ring 1258 that interacts with the limit switch actuator (as shown in FIG. 8 as element 808). When the basin 1200 is forced down upon temperature sensor 804, the indentation ring 1258 is able to move downward in the fluid warming device to depress the limit switch actuator to cause the limit switch (as described in connection with FIG. 7) to close and allow for the provision of energy to the heater.

Figure 15:
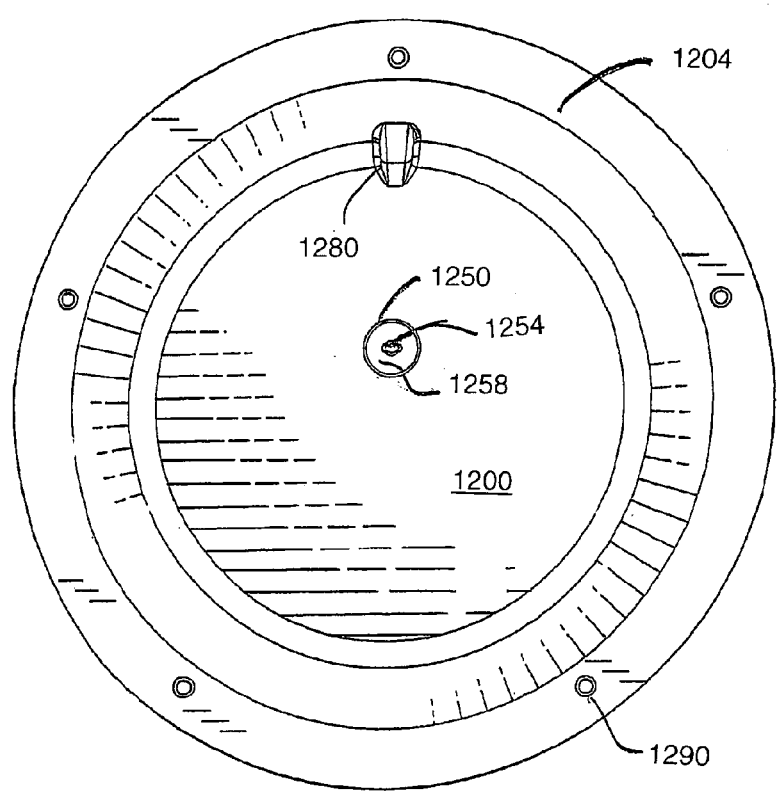

FIG. 15 is a top view of the same basin 1200. Alignment channel 1280 and thermocouple well 1250 extend into the bottom 1208 of the basin 1200 as shown in FIG. 14 but stick out into the fluid holding portion of the basin 1200 as shown in FIG. 15. FIG. 15 includes a top view of optional rim protrusions 1290 that protrude upward from the top face of the rim 1204

Figure 16:
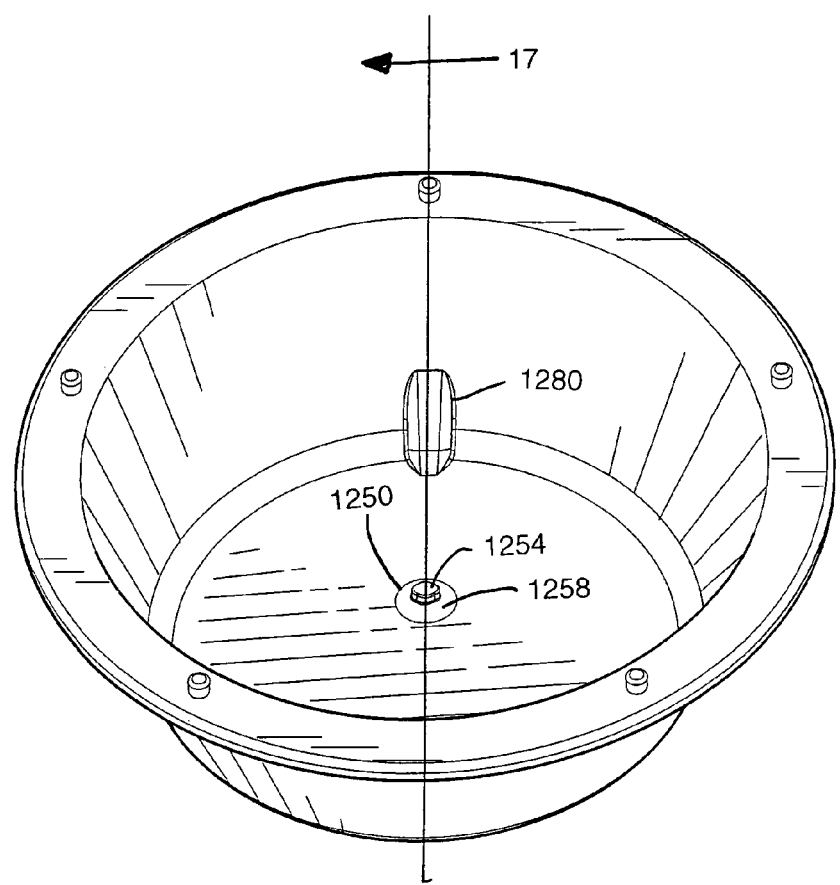
Figure 17:
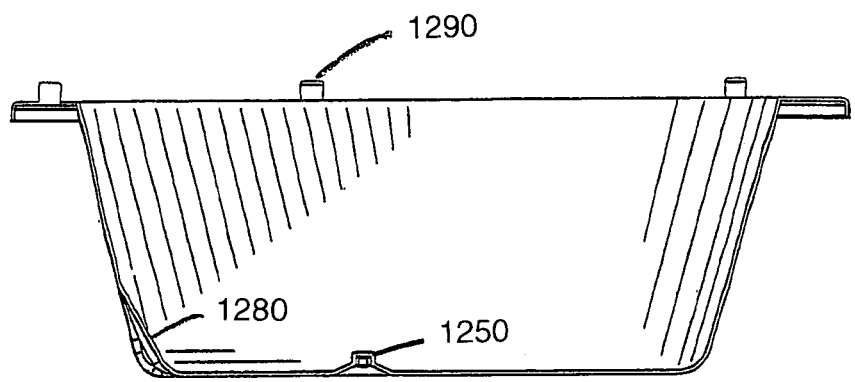
Figure 18:
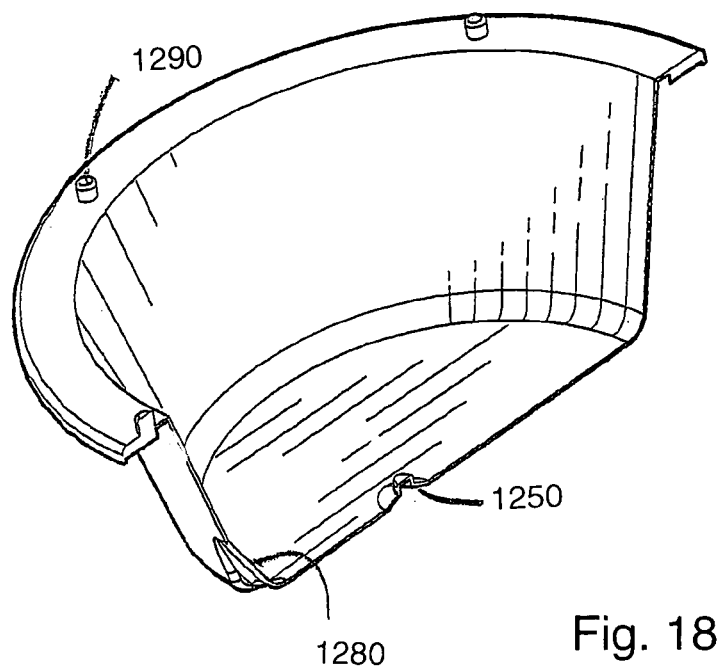

The extension of the thermocouple well 1250 into the basin is easier to see in FIG. 16 which shows a top and side perspective view of the basin 1200. The winged divot 1254 is seen extending above the indention ring 1258. A cross section taken through the alignment channel 1280, one of the five rim protrusions 1290, and the thermocouple well 1250 is shown in a side view in FIG. 17 and a top perspective view in FIG. 18.

The basin 1200 has the thermocouple well 1250 part way between the sidewall and the center of the basin. One of skill in the art will recognize that placement of the thermocouple well near the side walls of the basin is less likely to lead to obtaining a representative temperature of the fluid in the container as there is the possibility of edge effects impacting the measurement. However, one can appreciate that the function of the thermocouple well 1250 and the alignment channel 1280 could be combined by placing the temperature sensor and the limit switch actuator in the ridge that interacts with the alignment channel 1280 and eliminating the thermocouple well 1250 from the basin. While attractive from the standpoint of simplifying the basin, it is currently thought that a free-standing thermocouple well would provide a better indication of current fluid temperature.

Use of a Adapter

Figure 19:
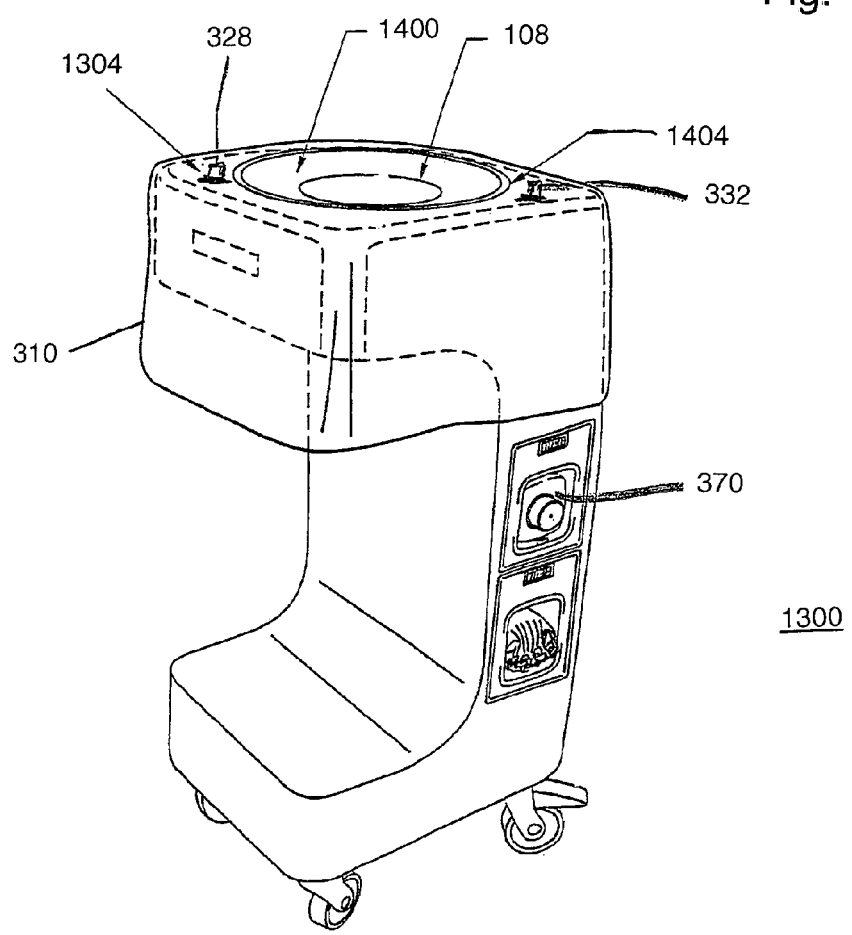
FIG. 19 is a top perspective view of an implementation of a liquid warming device 1300 with a removable container 1400 inserted into a cavity in the top face 1304 of liquid warming device 1300.

Turning now to FIG. 19, an implementation of a liquid warming device 1300 is presented through a top perspective view. Visible in this drawing is the liquid warming device 1300 with a removable container 1400 inserted into a cavity in the top face 1304 of liquid warming device 1300. The combination of the removable container 1400 and its container rim 1404 and a sterile drape 310 forms a sterile barrier above the upper portion of the liquid warming device 1300. Sterile fluid 108 is placed in the removable container 1400 and obscures from this view any thermocouple well or alignment channel which may be in use with this implementation. The removable container 1400 shown in FIG. 19 does not have the optional rim protrusions. Indicator lamps 328 and 332 are shown here visible through the drape 310, although the actual outlines of the lamps may be less recognizable through some surgical drapes as all that matters is that the indication can be accurately discerned through the surgical drape and the indication used in this implementation is the colored light selectively provided by the indicator lamps 328 and 332. A container of sterile fluid 370 is shown in an access sleeve as described in the above-identified application for Open Access Sleeve for Heated Fluid Units.

FIG. 20 is a top and side view of the components of interest from FIG. 19. FIG. 20A shows a top view without a removable container or sterile drape in place. The top surface 1304 had an opening 1308 to the cavity within the liquid warming device that receives the removable container. An optional alignment ridge 1312 is present in this implementation. The alignment ridge is adapted to interact with an alignment channel 1280 in a removable container. (FIGS. 12-18 contain an example of an alignment channel.) One of skill in the art will recognize that a variety of alignment ridges and alignment channels could be used to provide assistance to a user attempting to position the removable container so that it is in its intended alignment.

The limit switch configuration discussed in connection with FIG. 8 is shown in FIG. 20A with temperature sensor 804 surrounded by limit switch actuator 808, limit switch guide 888, insulating zone 812, and conductive material 816. As discussed in connection with FIG. 9, the limit switch actuator 808 interacts with the expected geometry around the thermocouple well 1250 as the temperature sensor 804 is placed in the thermocouple well 1250. Also visible are indicator lights 328 and 332.

In FIG. 20B, the removable container 1200 is included. The cross sectional side view shows the thermocouple well 1250 and the conductive material 816 but not the components of the temperature sensor and limit switch as the cross section is not taken through the thermocouple well. The cross section shows the indicator lamp 332 covered by sterile drape 310. The interaction of the container rim 1204, rest of the container 1200, and the sterile drape 310 serves to cover the top face 1304 so as to maintain the sterile field.

The removable container 1200 shown in FIG. 20 and discussed in the preceding text substantially fills the cavity in the liquid warming device. For example, the liquid warming device could be created to normally receive a six liter container. This liquid warming device may have an alignment ridge as shown in FIG. 20A to assist in placing the thermocouple well 1250 over the temperature sensor 804 and limit switch actuator 808. Heat passes to the sterile liquid placed in the interior of the container from a heater (not shown in FIG. 20) in thermal communication with conductive material 816.

The teachings of the present invention may be applied to create a liquid warming device that interacts with a larger or smaller container than those shown in the previous examples. The height to width aspect ratio of the container could be different than the containers used in the previous examples. Of course a single liquid warming device could have a large container cavity and a small container cavity with independent controls so that the surgical team could select to use either a large container, or a small container, or both a large and a small container.

While such a dual cavity liquid warming device would provide an adequate choice for the surgical staff on whether a large container or a small container would be best for the given surgical procedure, such a dual cavity liquid warming device would be more expensive than a liquid warming device with just one cavity for the traditional large container.

It would be advantageous for a single container liquid warming device to be able to adapt to provide controlled heat to a smaller container or other container as an alternative to the container that substantially fills the liquid warming device cavity.

A solution to this need is shown in FIG. 21. Top view of FIG. 21A shows a adapter 1500 placed on top of the liquid warming device. The adapter has a top level 1504 that rests on top of the top face 1304 of the liquid warming device. The adapter has a cavity with a recessed surface 1512 that is recessed relative to top level 1504. The boundary between the top level 1504 and recessed surface 1512 is shown here as irregular shape 1508. The irregular shape 1508 is partially circular as it stays within the opening 1308 of top surface 1304, but it does not need to be as large as opening 1308. Thus, some implementations of the adapter may opt to provide additional flat surface area 1520 that is at the same level as top level 1504. The adapter 1500 has an opening 1516 that exposes the temperature sensor 804, limit switch actuator 808, insulating zone 812, and conductive material 816.

Indicator lamps 328 and 332 are visible through the openings 1528 and 1532 in the adapter. Note that the tolerance between the indicator lamps and the openings may be much closer than shown in these conceptual drawings. If the indicator lamps have a frusto-conical shape, these can be used with a correspondingly shaped opening in the adapter to help precisely position the adapter 1500.

FIG. 21B shows a cross section taken through the center of small container 1550. Small container 1550 has its bottom 1562 resting on conductive material 816 so that heat may be conveyed from a heater to the container bottom 1562 as directed by the control system to heat sterile fluid placed in small removable container 1550. The combination of small container 1550, including rim 1554 and sterile drape 1540 sets up a barrier to isolate the top of the liquid warming device from the sterile field.

This sterile barrier is augmented by the container rim 1554 that extends out over the sterile drape 1540 so that there are two zones of interaction between the sterile container and the rim: A) the zone along the outside of the side wall 1522 of the container where the sterile drape 1540 engages the container, and B) the zone around the top of the container where the container rim 1554 extends out over the sterile drape 1540. As it is desirable for good thermal contact to be established between the bottom 1562 of the small container 1550 and the conducting material 816, it is useful for the side wall 1522 to be sufficiently tall to allow the container bottom 1562 to make contact with the conductive material 816 before the container rim 1554 makes contact with the draped adapter 1500.

The small removable container 1550 would be made to interact with temperature sensor 804 and limit switch 808 in the same manner as large removable container 1200. As best seen in FIG. 21A, this implementation of the adapter and small container interacts with the temperature sensor 804 and limit switch 808 as indicated by thermocouple well 1558 but does not interact with alignment ridge 1312 as the opening 1516 in the adapter is not over the alignment ridge 1312. The thermocouple well 1558 is shown here (and the other thermocouple wells shown in connection with this discussion of adapters) to represent its existence and not as a precise drawing of the actual shape and proportions of the thermocouple well as samples have been described above and what is important here is that the small container and adapter allow for the interaction of a small container with the same components of the liquid warming device that interact with the large container.

Other implementations of the adapter and corresponding small container could shift the opening in the adapter to be over all or a portion of the alignment ridge as long as the small container was adapted to provide the required spacing between any alignment channel (compare alignment channel 1280 in FIG. 16) and the thermocouple well.

In FIG. 22, the small container to be used with this adapter is smaller in diameter than a large container but the depth of the small container a approximately the same as the depth of the large container. In this case, the adapter 1600 shown in FIG. 22A covers the top surface of the liquid warming device while leaving indicator lamps 328 and 332 exposed through openings 1628 and 1632. The top surface 1604 of the adapter 1600 has opening 1616 over the temperature sensor 804 and limit switch actuator 808 but not over alignment ridge 1312.

FIG. 22B, a cross section taken through the midline of the small container 1650 again shows a thermocouple well 1658 visible at the cross section but not in the cross section. The bottom 1662 of the small container 1650 makes thermal contact with the conductive surface 816.

A sterile barrier is formed by the combination of sterile drape 1640 and the removable small container 1650. This sterile barrier is augmented by the container rim 1654 that extends out over the sterile drape 1640 so that there are two zones of interaction between the sterile container and the rim: A) the zone along the outside of the side wall 1622 of the container where the sterile drape 1640 engages the container, and B) the zone around the top of the container where the container rim 1654 extends out over the sterile drape 1640. As it is desirable for good thermal contact to be established between the bottom 1662 of the small container 1650 and the conducting material 816, it is useful for the side wall 1622 to be sufficiently tall to allow the container bottom 1662 to make contact with the conductive material 816 before the container rim 1654 makes contact with the draped adapter 1600.

FIG. 23A and FIG. 23B show another implementation of a adapter for using a container that is small in diameter but long in the sidewalls so that the "small" container is actually taller than the "large" container. FIG. 23A differs from FIG. 21A in that the elevation of recessed surface 1512 in FIG. 21A is below surface 1504 (including area 1520) in order to allow the bottom of the short container 1550 to make contact with the conductive material 816. In FIG. 23A, surface 1712 defined by perimeter 1708 is above surface 1704 (including area 1720) as surface 1712 is an elevated plateau. The elevated plateau 1712 has an opening 1716 above the temperature indicator 804 and limit switch actuator 808. The size and shape of elevated plateau 1712 can be just large enough to form a perimeter around the top of the container 1750 (shown in FIG. 23B) or can be substantially all of the adapter given the necessary adjustments for the indicator lamps 328 and 332. The decision with respect to the size of the elevated plateau may be influenced by the desirability of having a work surface at the plateau 1712 versus having more work surface at surface 1704 (including area 1720).

Turning to FIG. 23B, a cross section of tall removable container 1750 shows a representation of a thermocouple well 1758. Sterile drape 1740 engages side wall 1722 around the perimeter of container 1750 to help preserve the sterile barrier between the liquid warming device and the sterile field above the liquid warming device and the adapter 1700. In this implementation the container rim 1754 extends radially outward to cover the opening 1716 in the adapter but does not rest on the draped adapter plateau 1712. Container bottom 1762 is in thermal contact with conducting surface 816.

It may be desirable in some implementations to attach the adapter to a liquid warming device to allow the adapter to be placed in position for use or moved to a second storage position so that a large container that substantially fills the container cavity could be used. Alternatively, a frequently used adapter could be attached to the liquid warming device so that is readily available but a second adapter could be used for a less frequently used container when the attached adapter is moved to a stored position.

A piano hinge or other hinge allowing sufficient travel the adapter may be used to allow the small container to be rotated from an in-use position to a storage position. To the extent that adapter has either a recessed level or an elevated plateau, then the adapter will not lie flat against a flat panel side of the liquid warming device.

Care must be taken not to obstruct the view or access to any liquid warming device display or input device on any exterior surface of the liquid warming device.

Alternatively, a mechanism based on that used in fold down writing surfaces for use in auditoriums and lecture halls could be used to fold an attached adapter out of the way (again after making allowances for any recessed or elevated surfaces).

Unregulated Second Container

Another implementation of the present invention is to use a adapter as described above to place a container in proximity with temperature sensor and container detecting system (if any) as described above. This monitored container would be the one that triggers the control system to apply energy to the heater to provide additional heat to the conductive material. This process will lead to the sterile fluid in the monitored container being at or close to the target temperature. In this alternative implementation, one or more additional containers (unmonitored containers) would interact with the small container and surgical drape as described above, but would interact with the cavity in the liquid warming device through contact with the conductive material and would not interact with a temperature sensor. Thus, if sterile fluid below the target temperature was added to an unmonitored container but the monitored container had sterile fluid already at the target temperature, the liquid warming device would not react to the addition of the sub-target sterile fluid in the unmonitored container.

This unmonitored container would tend to be used to keep tools in the vicinity of the target temperature or other uses that are less sensitive to small variations from the target temperature.

Additional Implementations

One of skill in the art will recognize the ability to replace control devices acting as independent components such as limit switch 604 with components that feed data to a logic device that prevents power from going to the heater unless the data is beyond a threshold or in a range. Such replacements are deemed within the scope of the present invention.

While the examples of containers for use with the liquid warming device used containers with circular cross sections, other container geometries could be implemented. While circular basins are one common container shape found in hospital settings, other shapes can be used. The cavity in the liquid warming device would ideally be shaped in a like manner as the container bottom. Likewise a adapter could adapt a large cavity to receive a smaller container with a different cross section shape than used in the large cavity.

The invention may be implemented by integrating the drape and the container before inserting the combination into the fluid warming device, and most preferably, to integrate the two components into a single supplied component for use in the surgery before delivery to the operating room. However, it is a viable alternative to use a drape with an opening suitable to allow the container to interact with the various components of the liquid warming device yet combine with the drape to isolate the top of the liquid warming device from the sterile field. Optionally, the drape could attach to the top of the liquid warming device or to the walls of the cavity in the liquid warming device before the insertion of the container. As the drape will only be positioned on the liquid warming device for a moment until the container is placed through the hole in the drape, the drape would not have to be attached to either the container or the liquid warming device as it could simply be held in place until the container is inserted.

One of skill in the art will recognize that alternative implementations set forth above are not universally mutually exclusive and that in some cases alternative implementations can be created that implement two or more of the variations described above. In a like manner, one of skill in the art will recognize that certain aspects of the present invention can be implemented without implementing all of the teachings illustrated in any of the various disclosed implementations. Such partial implementations of the teachings of the present invention fall within the claimed subject matter unless the claims are explicit in calling for the presence of additional elements from other teachings.

For example, the discussion set forth above suggested a location for placement of the temperature sensor into a thermocouple well protruding out into the fluid to be measured. The present invention has many aspects and one could place a temperature sensor that was in another location such as contacting the bottom or side of the container (perhaps augmented through use of a spring to ensure solid contact) and still use other claimed aspects of the present invention.

In order to promote clarity in the description, common terminology for components is used. The use of a specific term for a component suitable for carrying out some purpose within the disclosed invention should be construed as including all technical equivalents which operate to achieve the same purpose, whether or not the internal operation of the named component and the alternative component use the same principles. The use of such specificity to provide clarity should not be misconstrued as limiting the scope of the disclosure to the named component unless the limitation is made explicit in the description or the claims that follow.

In order to make it easier for a reader to find certain sections of this document that are of particular interest to the reader, a series of headings have been used. These headings are solely for the purpose of helping readers navigate the document and do not serve to limit the relevance of any particular section to exclusively the topic listed in the heading.

Those skilled in the art will recognize that the methods and apparatus of the present invention have many applications and that the present invention is not limited to the specific examples given to promote understanding of the present invention. Moreover, the scope of the present invention covers the range of variations, modifications, and substitutes for the system components described herein, as would be known to those of skill in the art.

The legal limitations of the scope of the claimed invention are set forth in the claims that follow and extend to cover their legal equivalencies. Those unfamiliar with the legal tests for equivalency should consult with a person registered to practice before the United States Patent and Trademark Office.

What is claimed is:

1. An adapter for use in a particular liquid warming device, the particular liquid warming device designed for applying heat to a container that fits through an opening with a first cross sectional area in a top surface of the liquid warming device above a cavity in the liquid warming device, the adapter comprising:

a surface shaped to fit upon at least a portion of the top surface of the particular liquid warming device; and an opening in a portion of the adapter to be placed in a cavity in the particular liquid warming device such that the adapter may be placed upon the particular liquid warming device and receive a container through an opening in the portion of the adapter with a second cross sectional area, less than the first cross sectional area, to allow the container to receive direct heat input from the liquid warming device and thereby heat sterile fluid placed in the container;

wherein the adapter allows the container received through the opening with the second cross sectional area to be aligned with an alignment ridge present in the cavity of the particular liquid warming device; and wherein the adapter has a set of protrusions positioned to engage a set of rim protrusions on the container received through the opening with the second cross sectional area.

2. The adapter of claim 1 wherein the adapter allows the container received through the opening with the second cross sectional area to be placed in proximity to a temperature sensor that is used to measure temperature of sterile liquid in the container received through the opening with the first cross sectional area when the liquid warming device is used without the adapter such that sterile liquid in the container received through the opening with the second cross sectional area placed in the liquid warming device with the adapter in-use is monitored by the liquid warming device through the temperature sensor.

3. The adapter of claim 1 wherein the adapter allows the container received through the opening with the first cross sectional area to be placed in the cavity of the liquid warming device to actuate a limit switch that is used to note a presence of a container when the liquid warming device is used without the adapter such that the container received through the opening with the second cross sectional area placed in the liquid warming device with the adapter in-use satisfies the limit switch.

4. The adapter of claim 1 including a second opening that allows the adapter to be placed on the top of the liquid warming device to surround but not obstruct at least one indicator light.

5. An adapter for use in a liquid warming device, the liquid warming device designed for applying heat to a container received through an opening in a top of the liquid warming device above a cavity in the liquid warming device, the opening having a first cross sectional area; the adapter comprising:
 a surface shaped to fit upon at least a portion of a top surface of a particular liquid warming device; and
 an adapter opening in a portion of the adapter to be placed in a cavity in the particular liquid warming device such that the adapter may be placed upon a particular liquid warming device and receive a container through the adapter opening with a second cross sectional area, less than the first cross sectional area, to allow the container to receive direct heat input from the liquid warming device and thereby heat sterile fluid placed in the container;
 wherein the adapter is hingedly connected to a portion of the top of the liquid warming device to allow the adapter to rotate from a non-in-use position which allows the liquid warming device to receive a container through the opening of the first cross sectional area to an in-use position which precludes the liquid warming device from receiving a container through the opening of the first cross sectional area into the liquid warming device cavity; and
 wherein the adapter has a set of protrusions positioned to engage a set of rim protrusions on a container through the adapter opening with a second cross sectional area.

6. The adapter of claim 5 wherein the adapter allows the container received through the opening of the first cross sectional area to be placed in proximity to a temperature sensor that is used to measure temperature of sterile liquid in the container received through the opening of the first cross sectional area when the liquid warming device is used without the adapter such that sterile liquid in the container received through the adapter opening with the second cross sectional area placed in the liquid warming device with the adapter is monitored by the liquid warming device through the temperature sensor.

7. A method of adapting a liquid warming device with an opening above a cavity to receive a container, the opening having a first cross sectional area, the method of adapting allowing an adapted liquid warming device to receive, monitor, and heat a container received through an opening in the adapter with a second cross sectional area, smaller than the first cross sectional area; the method comprising:
 placing an adapter over at least a portion of the liquid warming device with an opening in the adapter positioned in the cavity in the liquid warming device;
 placing at least a portion of a container with the second cross sectional area into the cavity in the liquid warming device through the opening in the adapter so that a means for providing direct heat to sterile liquid in a container having a first cross sectional area received by the liquid warming device without an adapter in-use may be used to provide direct heat to sterile fluid in the container with the second cross sectional area;
 wherein the opening is positioned to allow the container with the second cross sectional area to be aligned within the liquid warming device through interaction with an alignment ridge that is used to align a container having a first cross sectional area received by the liquid warming device without an adapter in-use; and
 wherein the opening is in proximity to a set of protrusions to allow the container with the second cross sectional area to be aligned with the set of protrusions on the adapter that engage a set of rim protrusions on the container with the second cross sectional area.

8. The method of claim 7 wherein the opening is positioned to allow the sterile liquid in the container with the second cross sectional area to be monitored by a temperature measurement device that is used to monitor the sterile liquid in the container having a first cross sectional area received by the liquid warming device without an adapter in-use.

9. The method of claim 8 wherein the opening is positioned to allow a thermocouple well in an exterior of the container with the second cross sectional area to become engaged with the distal end of the temperature measurement device.

10. The method of claim 7 wherein the opening is positioned to allow the container having a first cross sectional area to satisfy a limit switch that is used to detect the presence of a container with the second cross sectional area used in the liquid warming device when the liquid warming device is used without the adapter.

11. The method of claim 7 wherein the adapter is connected to the liquid warming device but may move relative to the liquid warming device to assume a no-in-use position that allows the liquid warming device to receive a container through the opening in the top of the liquid warming device of the first cross sectional area or to assume an in-use position that limits the liquid warming device to receiving containers sized to fit within the adapter opening with the second cross sectional area.

* * * * *